US009433734B2

United States Patent
Ambrosina et al.

(10) Patent No.: US 9,433,734 B2
(45) Date of Patent: Sep. 6, 2016

(54) FLUID FLOW MEASUREMENT AND CONTROL

(71) Applicants: Jesse E. Ambrosina, Topsfield, MA (US); Benjamin G. Powers, Portsmouth, NH (US); Ali Shajii, Weston, MA (US)

(72) Inventors: Jesse E. Ambrosina, Topsfield, MA (US); Benjamin G. Powers, Portsmouth, NH (US); Ali Shajii, Weston, MA (US)

(73) Assignee: IVENIX, INC., Amesbury, MA (US)

( * ) Notice: Subject to any disclaimer, the term of this patent is extended or adjusted under 35 U.S.C. 154(b) by 208 days.

(21) Appl. No.: 14/171,435

(22) Filed: Feb. 3, 2014

(65) Prior Publication Data

US 2014/0309617 A1 Oct. 16, 2014

Related U.S. Application Data

(60) Provisional application No. 61/761,109, filed on Feb. 5, 2013.

(51) Int. Cl.
| | |
|---|---|
| *A61M 5/168* | (2006.01) |
| *A61M 5/14* | (2006.01) |
| *A61M 5/172* | (2006.01) |
| *A61M 5/145* | (2006.01) |
| *A61M 5/142* | (2006.01) |
| *A61M 5/44* | (2006.01) |

(52) U.S. Cl.
CPC ....... *A61M 5/16886* (2013.01); *A61M 5/1408* (2013.01); *A61M 5/14224* (2013.01); *A61M 5/14593* (2013.01); *A61M 5/16809* (2013.01); *A61M 5/16827* (2013.01); *A61M 5/172* (2013.01); *A61M 5/44* (2013.01); *A61M 2005/14513* (2013.01); *A61M 2205/3331* (2013.01); *A61M 2205/3334* (2013.01); *A61M 2205/3368* (2013.01); *A61M 2205/50* (2013.01); *Y10T 137/0379* (2015.04)

(58) Field of Classification Search
CPC .................... A61M 5/16809; A61M 5/16886; A61M 5/14593; A61M 5/16827; A61M 2205/3331; A61M 5/1483; A61M 5/16804; G01F 1/34
USPC .......................................................... 73/861
See application file for complete search history.

(56) References Cited

U.S. PATENT DOCUMENTS

| | | | |
|---|---|---|---|
| 4,337,639 A | 7/1982 | Jackson | |
| 4,976,162 A | 12/1990 | Kamen | |
| 5,421,208 A | 6/1995 | Packard et al. | |

(Continued)

FOREIGN PATENT DOCUMENTS

WO 2009/094590 A1 7/2009

OTHER PUBLICATIONS

International search report, PCT/U.S. 2014/014467, May 19, 2014, pp. 4.

(Continued)

*Primary Examiner* — Freddie Kirkland, III
(74) *Attorney, Agent, or Firm* — Chapin Intellectual Property Law, LLC

(57) ABSTRACT

In accordance with another embodiment, a controller in a fluid delivery system initiates drawing fluid into a chamber of a diaphragm pump. During a delivery phase of pumping the fluid in the chamber to a target recipient, the controller applies pressure to the chamber. At multiple different times during the delivery phase, the controller temporarily discontinues application of the pressure to the chamber to calculate how much of the fluid in the chamber has been pumped to the target recipient.

27 Claims, 11 Drawing Sheets

(56) References Cited

U.S. PATENT DOCUMENTS

| | | | | |
|---|---|---|---|---|
| 5,474,683 | A * | 12/1995 | Bryant | A61M 1/28 210/103 |
| 6,604,908 | B1 | 8/2003 | Bryant et al. | |
| 7,654,982 | B2 | 2/2010 | Carlisle | |
| 8,197,439 | B2 * | 6/2012 | Wang | A61M 1/28 604/67 |
| 2009/0131863 | A1 | 5/2009 | Carlisle et al. | |
| 2011/0028937 | A1 * | 2/2011 | Powers | A61M 5/14224 604/500 |
| 2011/0071465 | A1 * | 3/2011 | Wang | A61M 1/28 604/67 |
| 2011/0168270 | A1 | 7/2011 | Carlisle | |
| 2011/0218486 | A1 | 9/2011 | Huitt et al. | |
| 2012/0123322 | A1 | 5/2012 | Scarpaci et al. | |
| 2012/0312726 | A1 | 12/2012 | Gagel | |
| 2014/0148757 | A1 * | 5/2014 | Ambrosina | A61M 5/38 604/67 |
| 2014/0216560 | A1 * | 8/2014 | Ambrosina | A61M 5/14593 137/12 |

OTHER PUBLICATIONS

Supplementary European Search Report, EP 14 74 9592, Jan. 19, 2016, pp. 9.

* cited by examiner

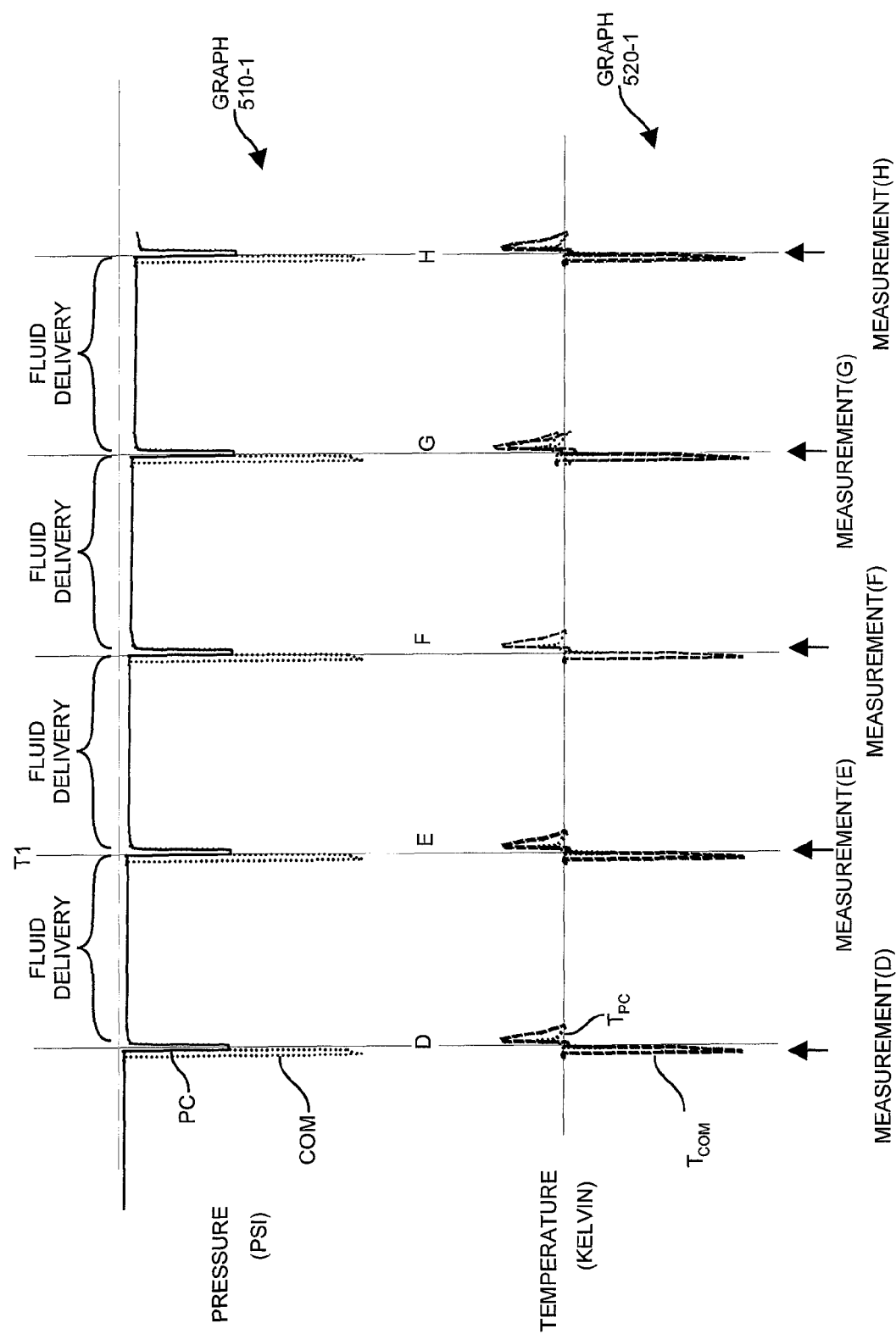

FLUID FLOW MEASUREMENT AND CONTROL

RELATED APPLICATIONS

This application claims the benefit of U.S. Provisional Patent Application Ser. No. 61/761,109 entitled "Measurement and Control of Fluid Flow in an Intravenous Pump," filed on Feb. 5, 2013, the entire teachings of which are incorporated herein by this reference.

BACKGROUND

Conventional techniques of delivering fluid to a recipient can include drawing a fluid from a fluid source into a chamber of a diaphragm pump. After the chamber is filled, a respective fluid delivery system applies a pressure to the chamber causing the fluid in the chamber to be delivered to a corresponding patient. The rate at which the fluid is delivered to the recipient may vary depending upon the magnitude of pressure applied to the chamber.

Eventually, after applying pressure to the chamber for a sufficient amount of time, all of the fluid in the chamber is delivered to the recipient.

In most applications, the amount of fluid drawn into the chamber of the diaphragm pump is substantially less than the amount of fluid to be delivered to the patient. To deliver the appropriate amount of fluid to the patient over time, the fluid delivery system repeats the cycle of drawing fluid from the fluid source into the chamber, and then applying pressure to the chamber to deliver the fluid to the recipient.

According to conventional techniques, based on the amount of elapsed time between time successive operations of drawing fluid into and expelling the fluid out of the chamber in the diaphragm pump, the fluid delivery system is able to determine the rate at which fluid is delivered to a corresponding patient.

BRIEF DESCRIPTION OF EMBODIMENTS

Embodiments herein are novel over conventional methods.
Temperature Estimation and Control More specifically, in accordance with first embodiments, a fluid delivery system includes a first volume (such as a first chamber) and a second volume (such as a second chamber). Assume that the first volume is of a known magnitude and that the second volume is of an unknown magnitude. In one embodiment, a controller in the fluid delivery system controls magnitudes of pressures in the first volume and the second volume to deliver fluid to a corresponding recipient.

To produce a more accurate measurement of fluid delivered to a recipient, the controller estimates a temperature of gas in the first volume and a temperature of gas in the second volume. The controller estimates the temperatures based on measurements of pressure in the first volume and measurements of pressure in the second volume. In other words, in one embodiment, the controller derives the estimated gas temperatures at least in part from the measurement of pressures in the first volume and the second volume.

In addition to estimating temperatures, the controller as described herein can be configured to calculate a magnitude of the second volume based on a combination of measured pressures and estimated temperatures of the gases in the first volume and the second volume.

In accordance with further embodiments, the fluid delivery system as described herein includes a valve disposed between the first volume and the second volume. The controller of the fluid delivery system initially closes the valve to prevent a transfer of gas between the first volume and the second volume. While the valve is closed, the controller controls a pressure of the first volume to be substantially dissimilar to a pressure of the second volume. During a measurement cycle of determining a size of the second volume, the controller opens the valve between the first volume and the second volume to enable a transfer of gas and to equalize the first volume and the second volume to substantially the same pressure. In accordance with further embodiments, the controller calculates the magnitude of the second volume based at least in part on measured pressures of the gases before and after opening the valve.

Thermal effects of the first volume and/or the second volume can have an impact on calculated volume. In accordance with yet further embodiments, to estimate the temperature of gas in the first volume and the temperature of gas in the second volume, the controller derives the estimated temperature of the gas in the first volume and the estimated temperature of the gas in the second volume based at least in part on thermal effects due to changes in pressure of the gases in the first volume and the second volume.

Physical attributes of the first volume and the second volume can affect respective actual and estimated gas temperatures of the gases. In accordance with further embodiments, when estimating the temperature of gas in the first volume and the temperature of gas in the second volume, the controller can be configured to derive the temperature of the gas in the first volume and the temperature of the gas in the second volume based at least in part on an estimated transfer of heat between the gases and respective physical boundaries defining the first volume and the second volume.

By further way of non-limiting example, note that the second volume can be a first chamber in a diaphragm pump. The diaphragm pump can include a second chamber disposed adjacent the first chamber. A flexible membrane in the diaphragm pump defines a boundary between the first chamber and second chamber. The controller controls a pressure applied to the first chamber (the second volume) to pump fluid in the second chamber to a target recipient. As described herein, the controller can apply negative pressure to the second volume to decrease a size of the second volume, drawing fluid into the second chamber of the diaphragm pump. The controller can apply positive pressure to the first chamber (second volume) to expel fluid from the second chamber of the diaphragm pump to a corresponding downstream recipient.

In accordance with still further embodiments, when the controller applies positive pressure to the second volume, the second volume changes over time as a result of delivering the fluid to the recipient. When estimating the temperature of gas in the first volume and the temperature of gas in the second volume, the controller can be configured to derive the temperature of the gas in the first volume and the temperature of the gas in the second volume based at least in part on a calculated change in the second volume over time.

In further embodiments, the controller uses the calculated magnitude of the second volume (volume of the first chamber in the diaphragm pump) to determine a flow rate of delivering fluid from the second chamber of the diaphragm pump to the target recipient.
Discontinuous Control Operation In accordance with second embodiments, a controller in a fluid delivery system initiates drawing fluid into a chamber of a diaphragm pump. During a delivery phase, the controller applies positive pressure to the chamber. The applied positive pressure pumps the fluid in the chamber to a target recipient. At one or more times during the delivery phase, the controller temporarily discontinues or interrupts application of a pressure to the chamber to calculate how much of the fluid in the chamber has been pumped to the target recipient.

More specifically, assume that the fluid delivery system first initiates filling a chamber in a diaphragm pump. The fluid delivery system exerts pressure on the chamber to deliver a portion of the fluid in the diaphragm pump to a downstream recipient. The fluid delivery system temporarily discontinues application of pressure to the chamber. In one embodiment, discontinuing application of the pressure includes reducing a pressure applied to the chamber. The reduced pressure causes pumping of the fluid in the chamber to the recipient to slow down or stop for a short amount of time. The time of the interruption of pressure may be so short that it is unnoticeable or insignificant.

During such time of temporarily discontinuing application of a pressure, the fluid delivery system calculates the amount of the fluid remaining in the chamber of the diaphragm pump.

After calculating the amount of fluid remaining in the chamber, the fluid delivery system applies pressure to the chamber again, (potentially the same or substantially similar pressure applied prior to the interruption) causing the fluid in the chamber to resume normal delivery of fluid to the recipient. In other words, resumption of applying the pressure to the chamber causes the fluid in the chamber to flow again to the recipient.

In one embodiment, the fluid delivery system repeats this process of discontinuing application of the pressure to the chamber to calculate an amount of fluid remaining in the chamber multiple times during a delivery phase. Multiple measurements enables the fluid delivery system to accurately detect an amount or flow of fluid to a recipient over time.

In yet further embodiments, as mentioned, the controller can be configured to apply a substantially constant pressure (before and after a step of temporarily discontinuing application of pressure) to the chamber to evacuate the fluid from the chamber into a respective conduit that conveys the fluid to the target recipient.

Using the calculated amount of fluid remaining in the chamber at different times during the delivery phase, the controller can calculate a flow rate of delivering the fluid in the chamber to the target recipient.

In accordance with further embodiments, the controller can be configured to compare the calculated flow rate to a desired flow rate such as a set point. In response to detecting that a difference between the calculated flow rate and the desired flow rate is greater than a threshold value, the controller can be configured to adjust a flow rate of the fluid from the chamber to the target recipient to be nearer to the desired flow rate.

Note that the controller can modify any suitable control parameter to adjust a flow rate of the fluid if it is different than a respective desired set point. For example, in one embodiment, the controller adjusts a magnitude of the pressure applied to the chamber during the delivery phase to increase or decrease the fluid delivery rate. Additionally or alternatively, the controller can be configured to adjust resistance of an in-line fluid flow resistor disposed between the chamber and the target recipient.

Discontinuing application of the drive pressure to the chamber can include controlling magnitudes of pressure in the chamber and a gas reservoir tank to be dissimilar. The reservoir tank can be a volume of known magnitude; the chamber can be a volume of unknown magnitude. In other words, as mentioned, the chamber can represent a varying volume, a magnitude of which varies as fluid is delivered to a recipient.

In further embodiments, the controller opens a valve between the reservoir tank and the chamber to substantially equalize a pressure of gas in the reservoir tank and the chamber. To more accurately calculate a rate of fluid delivery, as previously discussed, the controller can be configured to estimate a temperature of gas in the reservoir tank and a temperature of gas in the chamber based on a measured pressure in the reservoir tank and measured pressure of the chamber. The controller calculates how much fluid remains in the chamber based at least in part on measured pressures of the gases and the estimated temperatures of the gases in the reservoir tank and the chamber.

Also, as previously mentioned, the controller can be configured to calculate how much of the fluid has been pumped to the target recipient based at least in part on how much of the fluid drawn into the chamber remains in the chamber after applying positive pressure to the diaphragm pump.

These and other more specific embodiments are disclosed in more detail below.

Note that any of the resources as discussed herein can include one or more computerized devices, fluid delivery systems, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: control magnitudes of pressure in a first volume and a second volume, the first volume being of a known magnitude, the second volume being of an unknown magnitude;

estimate a temperature of gas in the first volume and a temperature of gas in the second volume based on measurements of pressure in the first volume and measurements of pressure in the second volume; and calculate a magnitude of the second volume based on measured pressures of the gases and estimated temperatures of gases in the first volume and the second volume.

Another embodiment herein includes a computer readable storage medium and/or system having instructions stored thereon. The instructions, when executed by computer processor hardware, cause the computer processor hardware to: initiate drawing fluid into a chamber of a diaphragm pump; during a delivery phase of pumping the fluid in the chamber to a target recipient, applying pressure to the chamber; and at multiple different times during the delivery phase, temporarily discontinuing application of the pressure to the chamber to calculate how much of the fluid in the chamber has been pumped to the target recipient.

Yet another embodiment herein includes a computer readable storage medium and/or system having instructions stored thereon. The instructions, when executed by computer processor hardware, cause the computer processor hardware to: control magnitudes of pressure in a first volume and a second volume to be dissimilar, the first volume being of a known magnitude, the second volume being of an unknown magnitude; initiate opening a valve between the first volume and the second volume to equalize a pressure in the first volume and the second volume; estimate a temperature of gas in the first volume and a temperature of gas in the second volume based on a measured pressure in the first volume and measured pressure of the second volume; and calculate a magnitude of the second volume based on measured pressures of the gases and estimated temperatures of the gases in the first volume and the second volume.

The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for use in delivering fluid to a recipient. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques.

For additional details and/or possible perspectives (permutations) of the invention(s), the reader is directed to the Detailed Description section and corresponding figures of the present disclosure as further discussed below.

BRIEF DESCRIPTION OF THE DRAWINGS

FIG. 5A is an example timing diagram illustrating application of different pressure to a diaphragm pump over time to deliver fluid to a target recipient according to embodiments herein.

Figure 1:
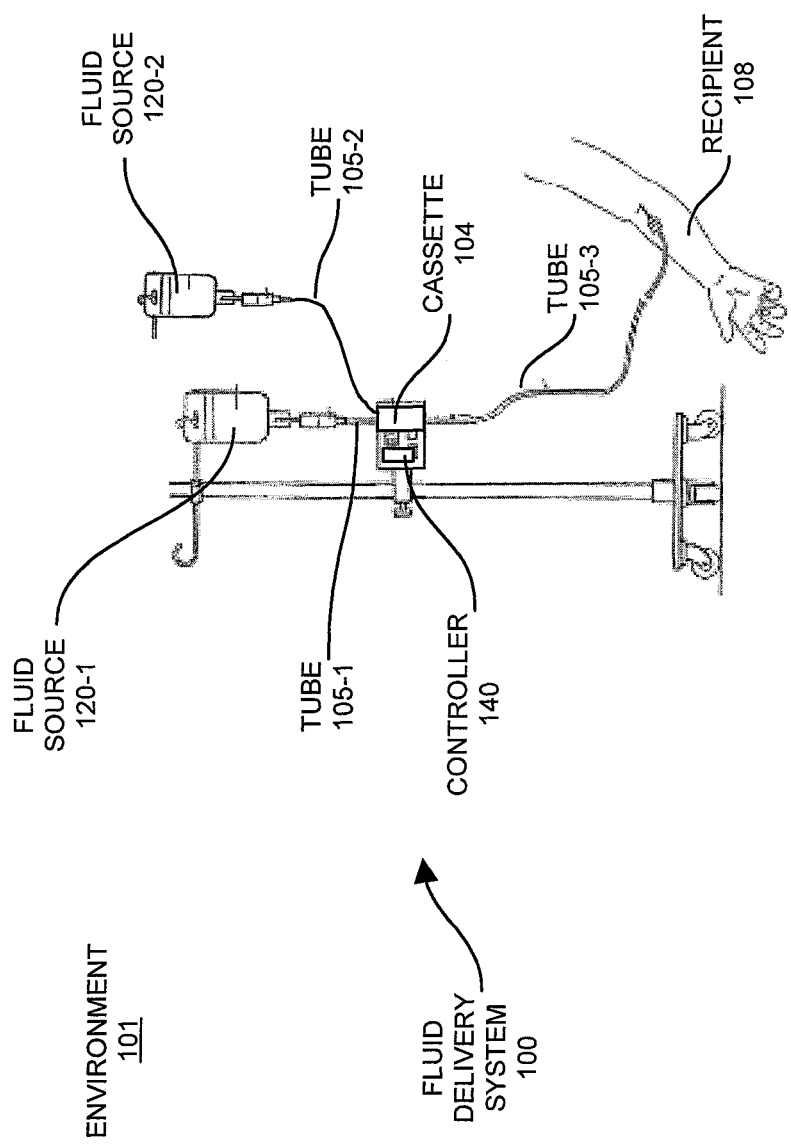
FIG. 1 is an example diagram illustrating a fluid delivery system according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

The fluid delivery system as described herein uses a system of valves, variable flow restrictions, reference volumes, direct pressure measurements, etc., to accurately deliver intravenous fluids to a recipient such as a patient. Typically fluids are introduced to the patient through a vein in the hand or arm. The pressure in the vein is typically on the order of 5 mm of Hg above atmosphere.

Conventional fluid pumps currently available in the market require that a respective fluid source be in a prescribed location with respect to the pump. Likewise, the pump must be in a prescribed location with respect to the patient. Variation in either source location or patient location can cause flow rate inaccuracy due to the affects of system pressure on the pumping mechanism. It is desirable for many reasons in a clinical setting for the pump to be able to deliver the fluid to the patient irrespective of the source fluid and pump position.

Embodiments herein use compressed gas (air) to induce the required differential pressures needed to move the fluid into the patient under a wide range of relative positions of the pump, the patient, and the fluid source. The fluid to be delivered may be below the patient or above the patient. The pump may be above or below the patient regardless of the fluid location. In certain instances, it is desirable that the fluid be delivered at as low a pressure as possible and at a continuous flow rate. The pump is able to use low pressure and accommodate a variety of relative pump and/or patient positions because the system can measure flow rate and adjust for any variations away from the target flow rate.

There are primarily two types of IV pumps on the market today; syringe and linear peristaltic pumps. Both are positive displacement pumps, which can present very high pressures to the patient in many circumstances. There are many limitations of this technology. As an example, in order to mitigate this risk, pressure sensors are added to detect dangerously high pressures and stop the pump. Due to the configuration of this technology and the elasticity of the tubing, large boluses of fluid are often injected to the patient inadvertently. In contrast, by using drive pressure directly to push the fluid to the patient rather than a rigid mechanical piston any disturbances stop the pump directly without the need for a detection system.

Now, more specifically, FIG. 1 is an example diagram illustrating a fluid delivery system according to embodiments herein.

As shown, fluid delivery environment 101 includes fluid delivery system 100. Fluid delivery system 100 includes fluid source 120-1, fluid source 120-2, and recipient 108. Fluid delivery system 100 includes controller 140 as well as cassette 104, facilitating delivery of fluid from one or more fluid sources 120 to the recipient 108.

In one embodiment, the cassette 104 is a disposable cartridge inserted into a cavity of a housing of the fluid delivery system 100. During delivery, fluid from the different fluid sources 120 is limited to contacting (disposable tube set including) cassette 104, tubes 103, and its corresponding components as further discussed below. When delivering fluid to a different patient, a caregiver inserts a new cassette into the cavity of fluid delivery system 100. The new cassette includes a corresponding set of new (sterile) tubes. Thus, the fluid delivery system 100 can be used for many patients without having to be cleaned.

As mentioned, during operation, the controller 140 of fluid delivery system 100 controls delivery of fluid from one or more fluid sources 120 (such as fluid source 120-1 and/or fluid source 120-2) to recipient 108. As shown in this example embodiment, tube 105-1 conveys fluid from fluid source 120-1 to cassette 104. Tube 105-2 conveys fluid from fluid source 120-2 to cassette 104. Note that fluid source 120-1 and fluid source 120-2 can store the same or different fluids.

The controller 140 controls one or more components in cassette 104 to deliver fluid received from fluid source 120-1 and/or fluid source 120-2 through tube 105-3 to recipient 108.

Control System:

By way of a non-limiting example, a mass flow based measurement system takes into account the ideal gas laws and mass conservation. The equations hold for a closed system.

$$M_{a1} + M_{b1} = M_{a2} + M_{b2} \quad \text{(equation 1)}$$

$$PV = MRT \rightarrow M = \frac{PV}{RT} \quad \text{(equation 2)}$$

R is a constant, so the equations factor down to:

$$\frac{P_{a1}}{T_{a1}}V_a + \frac{P_{b1}}{T_{b1}}V_b = \frac{P_{a2}}{T_{a2}}V_a + \frac{P_{b2}}{T_{b2}}V_b \quad \text{(equation 3)}$$

Estimation of temperatures as disclosed herein enables quick measurements and allows the device to operate without stopping the flow during measurements by taking into account the full system states (such as temperature), rather than assuming that they remain constant through the cycle.

More specifically, in one embodiment, an appropriate drive pressure can be applied to a drive chamber side of a diaphragm pump to initiate delivery of fluid in a fluid chamber side of the diaphragm pump to a target recipient. Further embodiments herein can include discontinuing application of the pressure to the drive chamber at one or more times during a delivery cycle to perform a volume check to identify how much of the fluid is present in the fluid chamber of the diaphragm pump over time.

In one embodiment, the flow rate of fluid pumped to a target recipient equals the change in volume of the drive chamber over time.

During times of discontinuing application of the pressure to the diaphragm pump, embodiments herein can include taking into account changes in temperature of the gases (as a result of changing pressures) in one or more chambers when calculating the flow rate of delivering the fluid to the target recipient.

In one embodiment, a mass balance measurement is dependent on the temperature of the working fluid. Given required measurement speed noted above, the gas experiences adiabatic heating and cooling during the measurement cycle. It may be difficult if not impossible to measure (with a temperature sensor) the gas temperature directly in the time frame needed; therefore a thermal estimator is used to predict the gas temperature. In other words, the temperature of gases in one or more volumes as discussed herein can change so quickly that a physical temperature sensor is unable to detect a respective change in temperature.

Figure 4:
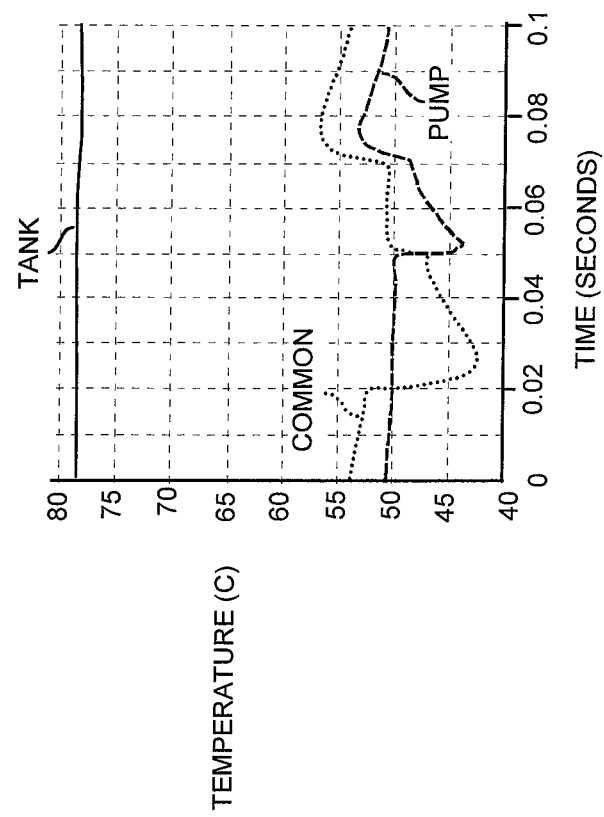
FIG. 4 is an example diagram illustrating a change in hypothetical gas temperatures during a fluid measurement cycle according to embodiments herein.

FIG. 4 is a hypothetical example diagram illustrating gas temperatures in different resources during a delivery cycle. As described herein, one or more temperatures can be estimated based on known system information as discussed in more detail below.

In one embodiment, there are several additions to the ideal gas law approach that are used to achieve the required performance characteristics for a safe and reliable infusion pump. First there are common conditions when the flow rate is low and the outlet pressure is low such as when the pump is significantly higher than the patient. In this case, the required drive or pumping pressure is also very low. Very low drive pressures are difficult to measure with common low cost pressure transducers and it is very difficult to accurately control and maintain low pressure in the positive tank. At higher flow rates or higher outlet pressure, the drive pressures needed are much higher. This wide dynamic range makes it difficult to maintain pressure measurement resolution.

In order to: i) achieve all of the desired flow rate range given the relatively wide range of outlet pressure, ii) maximize pressure measurement resolution, and iii) maintain a driving pressure high enough to avoid low pressure measurements near atmosphere, embodiments herein can include a variable flow restriction that is added downstream of the pump chamber.

By way of a non-limiting example, this flow restriction can be a variable orifice. Given a desired set point flow rate, the variable fluid restriction opening is changed to maintain a minimum drive pressure. This variable fluid restriction further serves as a safety mechanism that can be positively shut or closed if desired.

Another requirement of infusion systems may be to maintain continuous flow. In one embodiment, the fluid delivery system as discussed herein does not stop the pumping during a flow rate measurement. Thus, embodiments herein can include providing a continuous or substantially continuous flow of fluid delivery to a respective target recipient.

In order not to introduce measurement error, the volume measurement cycle can be performed extremely fast such as on the order of milliseconds. According to embodiments herein, a measurement cycle can be less than 200 milliseconds. The fill cycle, such as filling the chamber of the diaphragm pump with fluid, also can be performed very fast to minimize flow variation.

When the gases are moved at this high speed for all of the reasons above the isothermal Ideal Gas Law and Boyle's Law begin to breakdown. Specifically the assumption that the gas is isothermal is no longer true. It is observed that the gas experiences adiabatic heating and cooling during the measurement cycle. As previously discussed, embodiments herein include estimating gas temperatures to compensate for these errors.

In order to account for the temperature effects due to adiabatic heating and cooling of the gas the pressure and volume relationships are transformed as described above to yield:

$$V_{pc} = V_{com} \frac{\left(\frac{P_{com2}}{T_{com2}} - \frac{P_{com1}}{T_{com1}}\right)}{\left(\frac{P_{pc1}}{T_{pc1}} - \frac{P_{pc2}}{T_{pc2}}\right)} \quad \text{(equation 4)}$$

By way of a non-limiting example, the temperature can be estimated by tracking the system state variables at each time step of the control loop. The physical parameters of the delivery system, such as volume, orifice size, and heat transfer coefficients combined with the measured pressures allow the system to calculate an estimated temperature in each of the gas volumes at any point during the pumping cycle using the following energy balance equation:

$$\frac{dT_i}{dt} = \frac{1}{M_i C_v} \left[ C_p \sum_j T_j Q_{ji} - C_p T_i Q_{out} - C_v T_i (Q_{in} - Q_{out}) + H(T_{wall} - T_i) \right] - \left(\frac{C_p}{C_v} - 1\right) \cdot \frac{T_i}{V_i} \frac{dV_i}{dt} \quad \text{(equation 5)}$$

Where:
V=volume
Cv=specific heat at constant volume
Cp=specific heat at constant pressure
T=temperature
Q=mass flow
H=heat transfer coefficient Event Detection:

In order to avoid medication and other fluids delivery errors, the measurement and control systems typically must be able to quickly detect and in some cases automatically recover from a number of external disturbances. According to certain embodiments herein, the fluid delivery system 100 can quickly detect the following conditions:

When the fluid delivery path becomes occluded or kinked, peristaltic and mechanically actuated pumps continue trying to deliver fluid until a pressure sensor measures that drive pressure has exceeded a limit. This pressure is measured through the wall of the flow path tubing, and therefore must be set to a relatively high pressure. This can cause hazard to the patient or the release of a bolus of fluid when the occlusion is resolved. The fluid delivery system 100 as described herein can be configured to operate at a low drive pressure and monitor flow of liquid, rather than line pressure. As such, the system can simply detect a stop of flow and indicate to the user that an occlusion condition exists, without increasing drive pressure to an unsafe level or charging the fluid line with high-pressure liquid that can be released as a bolus.

An unexpected and sudden increase in the pressure from the source fluid can occur at any time. This can be induced by a patient or caregiver inadvertently squeezing or pressing on the bag, forcing fluid into the patient. According to embodiments herein, since the fluid delivery system 100 repeatedly and constantly monitors pressure, this condition can be detected, flow can be stopped, and an alarm can be activated.

Often medication is delivered in a small syringe by the caregiver by injecting the medication into the IV line via a Y-site or other access port. This small finite injection of fluid is referred to as a Bolus or "IV push". These actions are often not delivered over the correct amount of time or they are not recorded in the medical record in a timely manner. The fluid delivery system 100 as described herein can be configured to detect the pressure induced or the blockage of the line induced by the action of the caregiver injecting fluid into the line via a syringe.

The closed loop measurement and control system as employed by fluid source 100 is able to sense the difference in viscosity of the source fluid. Therefore it is able to discern the difference between different types of fluid for example the difference between blood, saline or saline mixed with Dextrose. According to yet further embodiments, the fluid delivery system 100 can be configured to differentiate between air in the source line or fluid in the source line. This ability to detect air can be used to more accurately calculate the total volume of fluid infused as well as enable a number of workflow advantages such as automatic detection of an empty source container and notifying the user appropriately.

Dose Correction:

A very common problem encountered during the administration of small doses of medication is that errors are induced due to the unknown volume of the tubing connecting the medication source and the patient. In some cases the contained volume of the tubing and administration set can be many times larger than the dose of the mediation delivered. Today, caregivers must either manually flush the line, pushing the dose through the tubing to the patient. Extra medication is provided by the pharmacy such that the correct dose can be delivered to the patient and the medication left in the volume of the tubing is thrown away or the incorrect dose is administered. Because the fluid delivery system 100 is closed loop and measures the volume of fluid being transferred directly and the contained volume of the administration set is known, the correct dose is delivered to the patient consistently. Furthermore, the current embodiment of the administration set (such as cassette and tubing) accommodates two inputs. One input can be used for the medication delivery via a syringe and the second input can be used to flush the line and push the dose through the tubing.

Secondary Administration Automation:

Most medications such as antibiotics are administered in combination with a primary fluid such as normal saline. This secondary or "piggyback" administration today requires that the caregiver position the secondary fluid container at a specific height relative to the primary. This method relies on gravity to function properly. Like the IV push or Bolus delivery, this is not recorded by the device thus requiring the caregiver to document the fluid delivery properly. The closed loop control and direct volumetric fluid measurement combined with a dual input administration set enables the complete automation of secondary fluid administration. According to certain embodiments herein, the fluid delivery system 100 is able to:

Deliver from syringe, or bag on secondary—intermittent or complete

Automatically switch between the primary fluid source 120-1 and secondary fluid source 120-2

Scheduled (i.e. time delay or intermittent) secondary

Deliver the secondary fluid without regard to the relative positions of the fluid sources, pump or patient Correctly and accurately deliver, measure and record all fluid delivery events

MORE DETAILED DESCRIPTION OF EMBODIMENTS

In one non-limiting example embodiment, the fluid pumping system as described herein is centered around a pumping chamber ("IPC"—Intermediate Pumping Chamber) that consists of a volume bifurcated by a flexible diaphragm. One side of the IPC is connected to the pneumatic portion of the fluidic system. The other side of the IPC is connected to the hydraulic portion of the fluidic system. Hydraulic pumping is achieved by applying alternating positive and negative pressure to the pneumatic side of the IPC, thus moving the diaphragm back and forth (or in and out).

Figure 2:
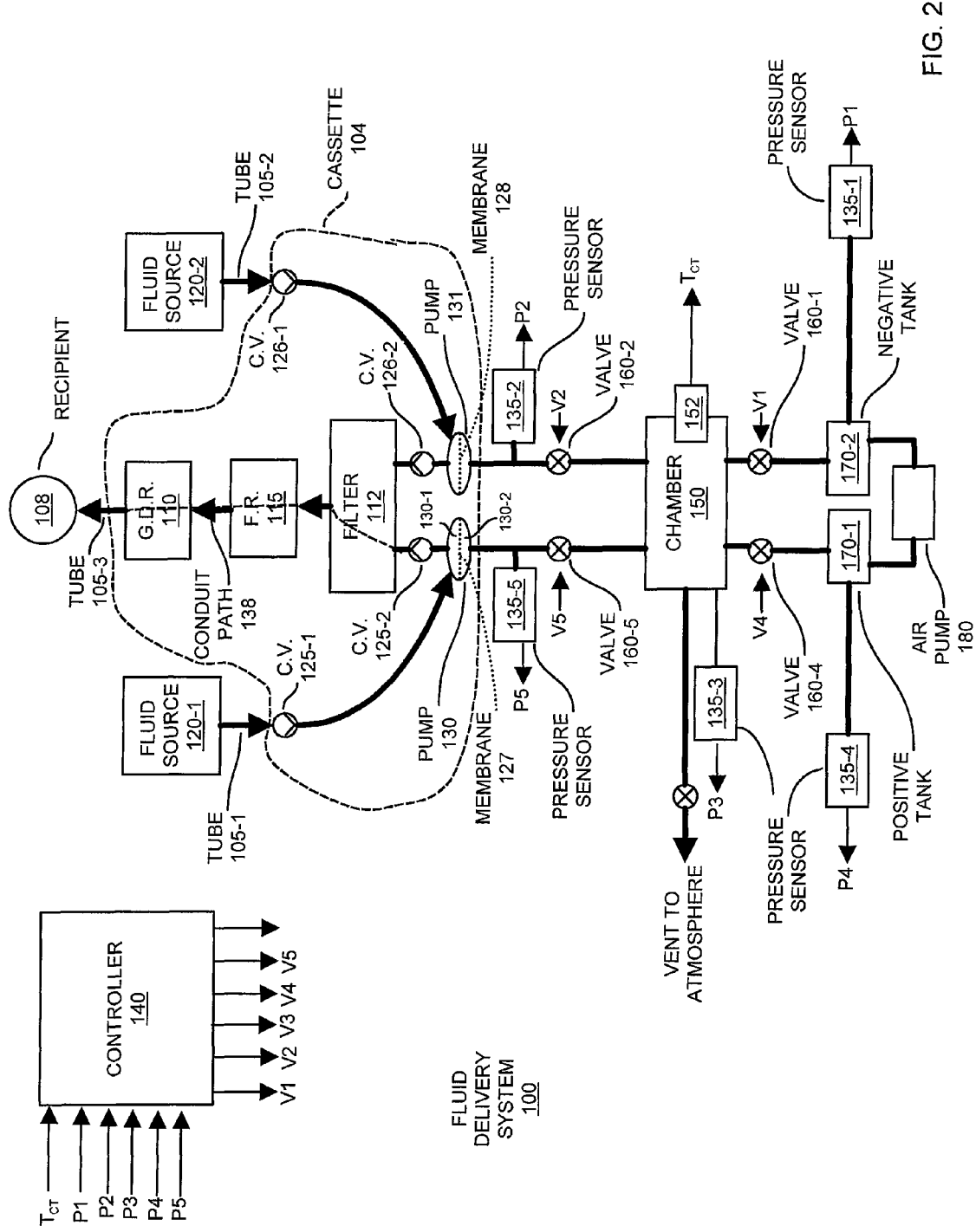
FIG. 2 is an example diagram illustrating more specific details of components and partitioning in a fluid delivery system according to embodiments herein.

FIG. 2 is a more specific example diagram illustrating components disposed in a fluid delivery system and corresponding disposable cassette according to embodiments herein.

As previously discussed, the controller 140 of the fluid delivery system 100 controls operation of diaphragm pumps 130 and 131 in disposable cassette 104 to precisely deliver fluid from one or more fluid sources such as fluid source 120-1 and fluid source 120-2 to a respective recipient 108.

In one embodiment, the flow of liquid through the system is controlled by adjustments to the drive pressure from the Positive Tank 170-1 and a variable hydraulic resistor (component such as fluid resistor 115) that is controlled by a motor or other suitable resource. Flow rate is measured using periodic volume calculations described below, and the control parameters are adjusted accordingly to drive the error between measured flow rate and target flow rate to zero.

Pump Cycle Overview

In accordance with yet further embodiments, a pump cycle is defined as a motion of drawing fluid into a diaphragm pump and then applying pressure to the diaphragm pump to deliver the fluid to a recipient. In accordance with a specific non-limiting example embodiment, a pump cycle can be defined as at least partially moving of the membrane 127 in the diaphragm pump 130 from one extreme (such as "full") to another extreme (such as "empty").

Figure 3:
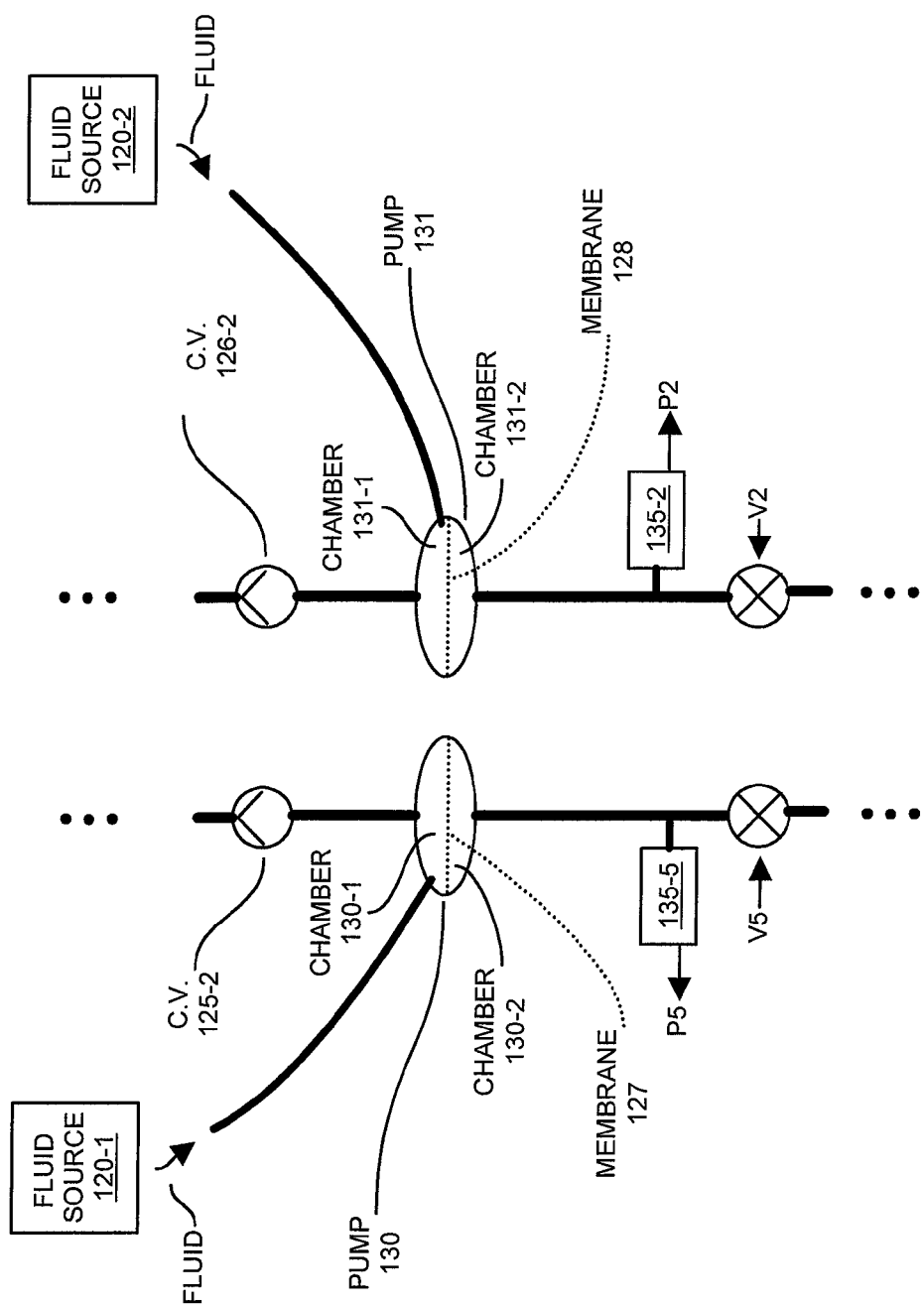
FIG. 3 is an example diagram illustrating details of a diaphragm pump used in a fluid delivery system according to embodiments herein.

As shown in FIG. 2 and more specific FIG. 3, membrane 127 divides the diaphragm pump 130 to include chamber 130-1 and chamber 130-2. Membrane 127 prevents fluid in chamber 130-1 from passing to chamber 130-2, and vice versa.

The membrane 127 dividing diaphragm pump 130 into chamber 130-1 and chamber 130-2 is flexible. When a negative pressure is applied to chamber 130-2, the volume of chamber 130-1 expands and draws fluid from fluid source 120-1 into chamber 130-1.

Conversely, when a positive pressure is applied to chamber 130-2, the volume of chamber 130-1 decreases expelling fluid from chamber 130-1 downstream to a respective recipient 108.

The total volume or capacity of chamber 130-1 and chamber 130-2 is substantially constant regardless of the position of the membrane 127. Based on knowing the volume of fluid in chamber 130-2, one is able to determine a corresponding volume of chamber 130-1. For example, if the total volume of the diaphragm pump 130 is Vtotal, and the volume of chamber 130-2 is V2, the fluid delivery system 100 can determine the volume of chamber 130-1 by subtracting V2 from Vtotal.

Diaphragm pump 131 operates in a similar manner as diaphragm pump 130. Membrane 128 divides the diaphragm pump 131 to include chamber 131-1 and chamber 131-2. Membrane 128 prevents fluid in chamber 131-1 from passing to chamber 131-2, and vice versa.

The membrane 128 dividing diaphragm pump 131 into chamber 131-1 and chamber 131-2 is flexible. When a negative pressure is applied to chamber 131-2, the chamber 131-1 draws fluid from fluid source 120-2 into chamber 131-1. Conversely, when a positive pressure is applied to chamber 131-2, the diaphragm pump 131 expels fluid from chamber 131-1 downstream to a respective recipient 108.

In a similar manner as previously discussed for diaphragm pump 130, the total volume or capacity of chamber 131-1 and chamber 131-2 is substantially constant regardless of the position of the membrane 128. Based on knowing the volume of fluid in chamber 131-2, the controller 140 is able to determine a corresponding volume of chamber 131-1. For example, if the total volume of the diaphragm pump 131 is Vtotal, and the volume of chamber 131-2 is determined as being V2, the fluid delivery system 100 can determine the volume of chamber 131-1 by subtracting V2 from Vtotal.

In this example embodiment, as shown in FIG. 2, temperature sensor 152 measures a temperature (e.g., TTC) of gas in chamber 150 (common tank) and provides a baseline from which to estimate the temperatures of gases in one or more of the following resources: chamber 150, pump chamber 130-2, positive tank 170-1, negative tank 170-2, etc.

As further discussed below, estimation of the temperature enables a more accurate assessment of how much of fluid in pump chamber 130-1 has been pumped in a direction towards the target recipient 108 over conduit path 138 (such as a path from diaphragm pump 130 through a combination of check valve 125-2, filter 112, fluid resistor 115, gas detection resource 110, and tube 105-3 to recipient 108).

Initially, to fill the chamber 130-1 with fluid from fluid source 120-1, the controller 140 of fluid delivery system 100 applies a negative pressure or vacuum to chamber 130-2. At such time, pump chamber 130-2 reduces in volume, causing the chamber 130-1 to fill with fluid received from fluid source 120-1 through check valve 125-1. Check valve 125-1 prevents fluid from flowing in a backward direction from diaphragm pump 130 to fluid source 120-1. Check valve 125-2 prevents fluid from flowing in a backward direction from conduit path 138 to the pump chamber 130-1.

Assume that prior to filling, the chamber 130-1 is substantially empty of fluid. In one embodiment, to draw fluid into chamber 130-1 with negative pressure from tank 170-2 as discussed above, the controller 140-1 generates respective control signals V1 and V5 to open valve 160-1 and 160-5 (while all other valves are closed) to draw fluid from fluid source 120-1 and check valve 125-1 into chamber 130-1.

Subsequent to chamber 130-1 being filled with fluid, the controller 140 controls settings of the valves 160 to apply a positive pressure from tank 170-1 to chamber 130-2 of diaphragm pump 130. For example, via generation of control signals V4 and V5, the controller 140 opens valves 160-4 and 160-5 and closes all other valves. The flow of gas from positive tank 170-1 to pump chamber 130-2 causes pumping of fluid from chamber 130-1 through check valve 125-2 along conduit path 138 to the target recipient 108. As previously discussed, during application of positive pressure o chamber 130-2, check valve 125-1 prevents fluid in chamber 130-1 from flowing back into fluid source 120-1.

As shown, the conduit path 138 through cassette 104 can include filter resource 112 that eliminates air and/or particulate matter in the fluid from being pumped to the target recipient 108.

Additionally conduit path 138 can include an in-line flow resistor 115. In one embodiment, the controller 140 utilizes the in-line flow resistor as one means to control a rate of delivering fluid to the target recipient 108. For example, at a given driving pressure in chamber 130-2, to decrease a rate of flow, the controller 140 increases a resistance of the in-line flow resistor 115. To increase a flow rate of fluid from the chamber 130-1 to the target recipient 108, the controller 140 decreases a resistance of the in-line flow resistor 115.

Note that drive pressure in chamber 130-2 is another way to control a rate of delivering fluid to the target recipient 108. At a given position of an in-line flow resistor 115, the controller can use air pump 180 and pressure gauge 135-4 to set a target drive pressure in positive tank 170-1. That drive pressure can then be applied to pump chamber 130-2 (by opening valve 160-5) to drive the fluid in chamber 130-1 to target recipient 108. To increase a flow rate of fluid from the chamber 130-1 to the target recipient 108, the controller 140 can be configured to increase the drive pressure in positive tank 170-1. To decrease a flow rate the controller 140 can be configured to decrease the drive pressure in positive tank 170-1.

Note that conduit path 138 also can include gas detector resource 110. The gas detector resource 110 can be configured to detect presence of air (or other gases) in the fluid being pumped through conduit path 138 to the target recipient 108. Based on feedback from the gas detector resource 110 as monitored by the controller 140, the controller 140 can be configured to sound an alarm in the event of detecting presence of gas in the fluid pumped to the target recipient 108.

During a delivery phase, the controller 140 can be configured to mainly apply pressure to chamber 130-2 with gas from tank 170-1 or tank 150 to cause the fluid in chamber 130-1 to be pumped to the target recipient 108. Delivery of the fluid in chamber 130-1 through conduit path 138 to target recipient 108 can be controlled by the controller 140 in accordance with a pre-selected fluid delivery rate. In other words, the controller 140 controls positive pressure applied chamber 130-1 to control a respective fluid flow rate. As further discussed below, embodiments herein can include at least temporarily discontinuing application of pressure to chamber 130-2 in order to perform a measurement of fluid remaining in chamber 130-1. As shown and discussed, discontinuing application of pressure to chamber 130-2 can at least temporarily reducing a pressure in chamber 130-2.

During a fluid delivery phase, the controller 140 supplies a substantially constant pressure to the chamber 130-2. Because the membrane 127 is flexible, the pressure in chamber 130-2 exerts a force on the fluid in chamber 130-1. In general, via application of the appropriate pressure to chamber 130-2, the controller 140 is able to fairly accurately pump the fluid at a desired flow rate. However, in certain situations, the delivery system 100 can be perturbed, resulting in errors in the flow rate. For example, as previously mentioned, the fluid source 120-1 may be squeezed, the elevation of fluid source 120-1 may change, etc. Any of these conditions can impact an accuracy of a desired fluid delivery rate.

Note that in addition to applying positive pressure to the pump chamber 130-2 during a fluid delivery phase, embodiments herein can include occasionally checking how much of the fluid drawn into the chamber 130-1 has been pumped towards the target recipient 108 through conduit path 138. This enables the controller 140 to accurately determine the actual flow rate of fluid, even during times when the system conditions are perturbed.

More specifically, one way to measure a fluid delivery rate during a respective delivery phase is to repeatedly measure how much of the fluid in the chamber 130-1 has been pumped towards target recipient 108 on conduit path 138 at one or more MEASUREMENT times during the delivery phase. For example, the controller 140 the controller can initiate checking the volume of gas in chamber 130-2 over multiple sample times of a positive pressure delivery cycle. Because it is known how much gas is initially in the chamber 130-2 at the beginning of a delivery phase, and based on calculating how much gas is in chamber 130-2 at different times, etc., the controller is able to accurately measure a rate of pumping or delivering the fluid from fluid source 120-1 over conduit path 138 to the target recipient 108 in between times of filling the chamber 130-2. Thus, the controller 140 is able to accurately measure fluid delivery in very small increments of time between successive cycles of refilling the chamber 130-1 with additional fluid.

In one embodiment, as previously discussed, the total volume of the diaphragm pump 120-1 including chamber 130-1, chamber 130-2 and conduit there between is a known quantity. One embodiment herein includes calculating how much fluid remains in chamber 130-1 based on knowing the volume of chamber 130-2. That is, the volume of the chamber 130-1 can be calculated by subtracting the volume of chamber 130-1 from the total volume of diaphragm pump 130. As discussed below, the volume of chamber 130-2 is initially an unknown quantity but is calculated based on pressure and estimated temperature.

FIG. 5A is an example diagram illustrating fluid measurements during fluid delivery according to embodiments herein. As shown, graph 510-1 illustrates application of pressure for more than 95% of a delivery cycle. PC represents the pressure of gas in chamber 130-2; COM represents the pressure of gas in the chamber 150.

In between times of applying pressure to chamber 130-2 (such as times labeled as FLUID DELIVERY), the controller 140 of fluid delivery system 100 periodically or occasionally, at multiple times, performs a measurement (labeled as MEASUREMENT) to determine a volume of chamber 130-2 of diaphragm pump 130. By way of non-limiting example embodiment, the controller 140 initiates applying an approximately constant pressure during FLUID DELIVERY portions of a fluid delivery cycle while the applied pressure to chamber 130-2 is reduced briefly during each respective MEASUREMENT.

In this example embodiment, graph 520-1 illustrates changes in temperature of respective gases that occur during each of the measurements. For example, Tcom represents the estimated temperature of the gas in the chamber 150; Tpc represents the temperature of gas in the chamber 130-2.

In general, in one non-limiting example embodiment, the duty cycle of performing measurements versus delivering fluid is relatively small. That is, in one non-limiting example embodiment, most of a fluid delivery cycle (delivery phase) can be used to deliver corresponding fluid in chamber 130-1 of pump 130 to recipient 108. For a small portion of the delivery cycle, the controller 140 operates respective resources to perform a corresponding volume MEASUREMENT of the chamber 130-2 as shown. Recall that after a volume of the chamber 130-2 is known, the volume of chamber 130-1 can easily be determined.

Figure 5B:
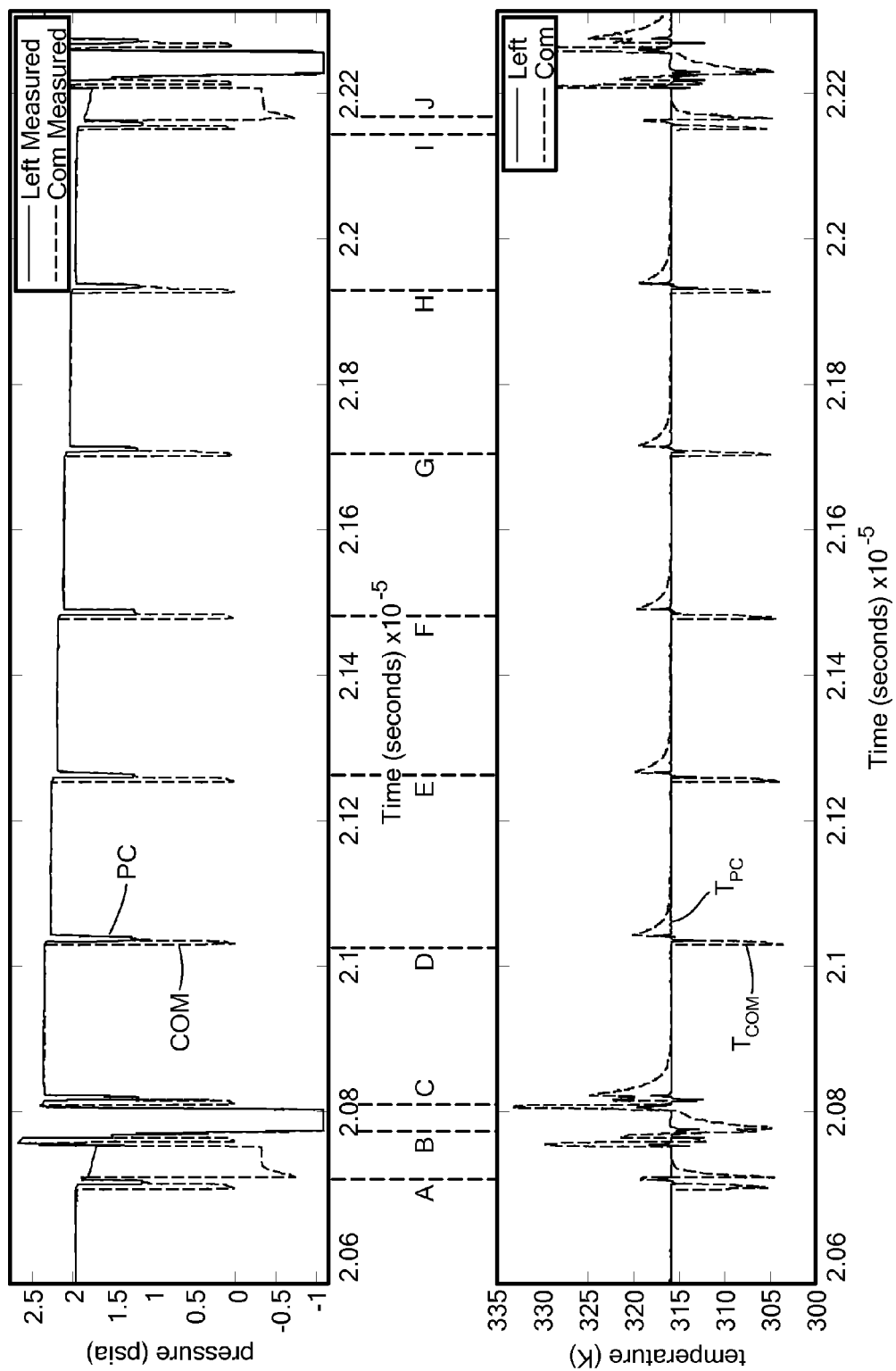
FIG. 5B is an example timing diagram illustrating application of different pressure to a diaphragm pump over time to deliver fluid to a target recipient according to embodiments herein.

FIG. 5B is an example diagram illustrating more particular details of a fluid delivery cycle according to embodiments herein.

Graph 510-2 shows the pressures measured in the system during a fluid delivery cycle. Graph 520-2 shows the estimated temperatures measured in the system during a fluid delivery cycle.

For the discussion here, the focus will be on pumping from the left hydraulic channel (e.g., from fluid source 120-1, through check valve 125-1, to diaphragm pump 130, through conduit path 138 to the target recipient 108), but the same patterns, behaviors and measurements apply to the right channel (e.g., from fluid source 120-2, through check valve 125-2, to diaphragm pump 131, to the target recipient 108) as well.

As previously discussed, one or more diaphragm pumps can be operated in any suitable manner to deliver one or more fluids to a target recipient 108. For example, the controller 140 can individually and accurately control the flow rate of each of the fluids delivered to the target recipient 108.

In one non-limiting example embodiment, the controller 140 can pump a first fluid from fluid source 120-1 to the target recipient 108 at a first fluid delivery rate; the controller 140 can pump a second fluid from fluid source 120-2 to the target recipient 108 at a second fluid delivery rate, the first delivery rate can be different than the second delivery rate.

At or around time [A] in FIG. 5B, a delivery cycle begins by resetting the pressures in the positive tank 170-1 and negative tank 170-2. The controller 140 sets the solenoid valves 165-1, 165-2, 165-3, 165-4, and 165-5 (via generation of control signals V1, V2, V3, V4, and V5) to a closed position. The controller 140 activates (turns ON) air pump 180 to bring the tanks to the desired drive pressure.

At time [B], valves 160-1 (V1) and 160-5 (V5) are opened to apply the pressure in the negative tank 170-2 to the chamber 130-2. The negative pressure draws the diaphragm membrane 127 back towards tank 150, filling chamber 130-1 with fluid from fluid source 120-1. Check valve 125-1 (CV1) opens due to the differential pressure. Fluid such as liquid from fluid source 120-1 is drawn into the chamber 130-1 of the diaphragm pump 130.

At time [C] valves 160-4 (via generation of signal V4) and 160-5 (via generation of signal V5) are opened to apply the pressure in the positive tank 170-1 to the chamber 130-2 of the diaphragm pump 130. The positive pressure causes check valve 125-1 (CV1) to close and check valve 125-2 (CV2) to open. This causes the liquid in the chamber 130-2 of the diaphragm pump 130 to flow on conduit path 138 towards the target recipient 108 such as a patient.

In one embodiment, some time after the chamber 130-2 of diaphragm pump 130 is brought to positive pressure, the controller 140 performs volume calculations such as at times [D], [E], [F], etc. Aspects of the volume calculation are discussed in more detail below. As previously discussed, one or more volume calculations can be performed periodically during the time that the chamber 130-1 is emptying (e.g., during times [C] through [I]).

After the last volume measurement at time [I], or at any time during the delivery phase, the controller 140 calculates a flow rate from the volume measurements. Based on the calculated flow rate the controller 140 can determine if adjustments are needed to one or both of the two flow control parameters: target drive pressure in positive tank 170-1, in-line fluid resistance 115.

In general, increasing the pressure of gas in the chamber 130-2 of the diaphragm pump 130 increases the rate of fluid delivery; decreasing a magnitude of gas pressure applied to chamber 130-2 decreases a respective rate of fluid delivery.

Additionally, increasing an amount of fluid resistance provided by fluid resistor 115 reduces a rate at which the fluid in chamber 130-1 is delivered to the recipient 108; decreasing amount of fluid resistance provided by fluid resistor 115 increases a rate at which the fluid chamber 130-1 is delivered to the recipient 108.

The fluid delivery cycle restarts when the air pump 180 is turned on at time [J] to reset the pressures in the positive tank 170-1 and negative tank 170-2 again.

Measure Cycle Overview

Figure 6:
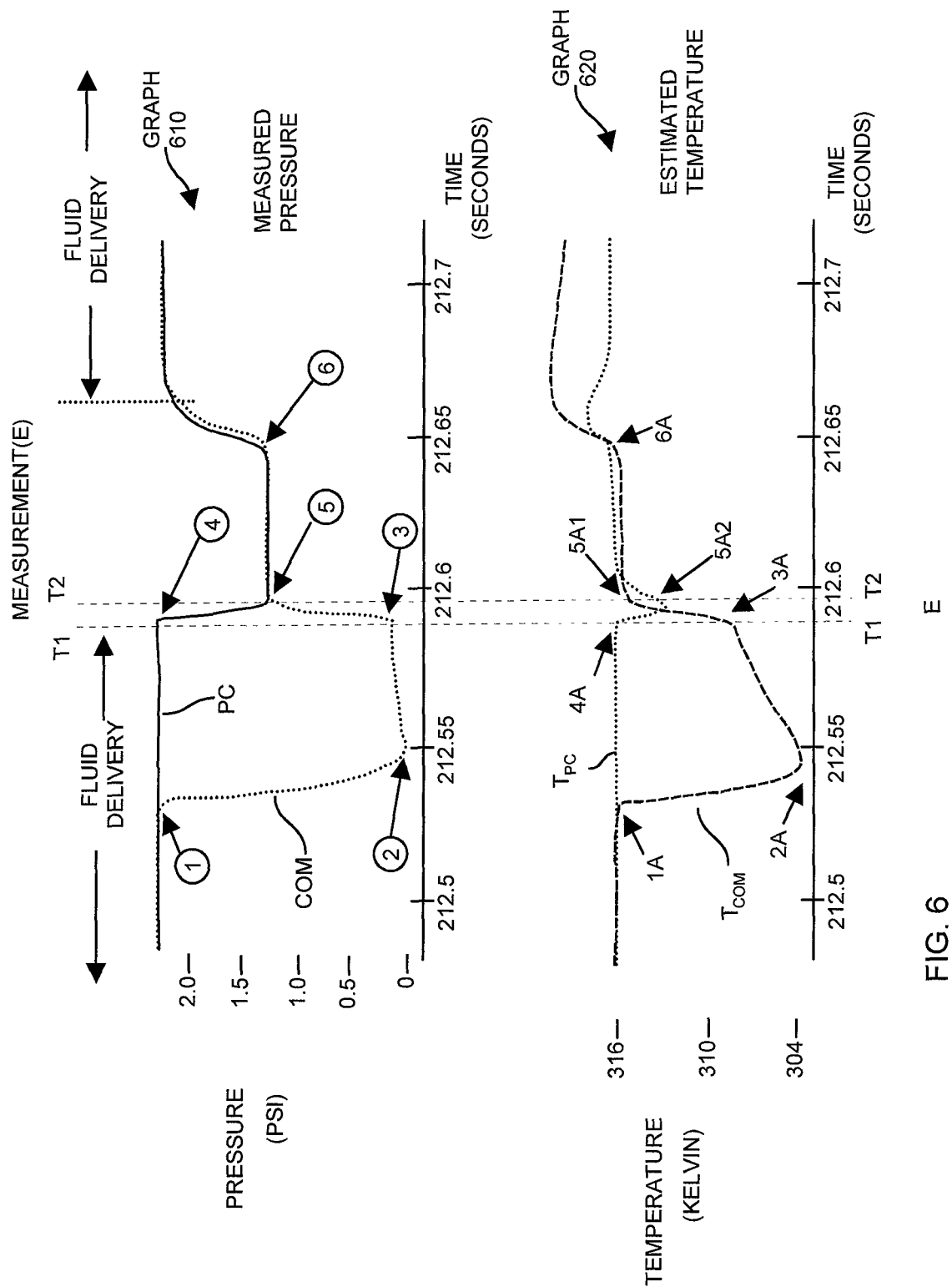
FIG. 6 is an example timing diagram illustrating temporary termination or reduction of applying positive pressure to a diaphragm pump and estimation of gas temperatures according to embodiments herein.

FIG. 6 is an example diagram illustrating a MEASUREMENT (time E) during a fluid delivery cycle according to embodiments herein.

Graph 610 illustrates gas pressures in each of multiple volumes. In this example embodiment, the pressure signal labeled PC in graph 610 represents the pressure of a gas in chamber 130-2 as measured by pressure sensor 135-5 (which produces pressure signal P5). The pressure signal labeled COM in graph 610 represents the pressure of a gas in chamber 150 as measured by pressure sensor 135-3 (which produces pressure signal P3).

Graph 620 illustrates estimated temperatures of the respective gases in the chamber 150 and chamber 130-2.

At the start of a respective fluid delivery cycle, the chamber 150 (Common Tank), positive tank 170-1, and the diaphragm pump 130 (e.g., Left IPC) are all at to the same pressure such as the driving pressure of the system. The driving pressure represents the pressure of the gas applied to chamber 130-2 prior to time T1.

At point [1] in graph 610, the controller 140 generates control signals V1, V2, V3, etc., to close all of the valves 160 to isolate the gas volumes. The controller controls valve 160-3 (via signal V3) to an open state to vent the chamber 150 (Common Tank) to ambient pressure.

When the pressure in the chamber 150 reaches ambient pressure at approximately point [2], the controller 140 controls valve 160-3 (via generation of signal V3) to a closed position again such that all of the gas volumes are again isolated.

After a brief stabilization period (such as approx. 50 milliseconds), at approximately time, T1, (shown as points [3] and [4]), the controller 140 controls valve 160-5 (via generation of signal V5) to an open state to merge the gas in chamber 130-2 with the gas in chamber 150. The gas pressure in the chamber 130-2 and tank 150 equalize at or around point [5] in graph 610. In one embodiment, the volume of chamber 130-2 and chamber 150 are approximately the same. In this example embodiment, opening of valve 160-5 causes the pressure in the chamber 130-2 to reduce by approximately 50%. The amount of reduction in pressure applied to chamber 130-2 varies depending on a volume of chamber 130-2 and a volume of chamber 150.

After another brief stabilization period (such as approx. 50 milliseconds or at point [6]), the controller 140 controls valve 160-4 (via generation of signal V4) to an open state to connect the chamber 130-2 (Left IPC) and the chamber 150 to the positive tank 170-1 to bring all three gas volumes up to the driving pressure again, during which the pressure in the chamber 130-2 causes the chamber 130-1 to pump respective fluid to the target recipient 108. Thus, embodiments herein include at least temporarily discontinuing application of the drive pressure in order to obtain pressure measurements at different times.

In one embodiment, the actual volume calculation produced by the controller 140 occurs based on measurements of pressure collected by the controller 140 at or around points [3], [4], and [5].

At substantially time T1 or point [3], the controller 140 receives signal P5 generated by pressure sensor 135-5 to determine the pressure Ppc of the gas applied to chamber 130-2.

At substantially time T1 or point [4], the controller 140 receives signal P3 generated by pressure sensor 135-3 to determine the pressure Pcom of the gas in chamber 150.

At substantially time T2 or point [5], the controller 140 receives signal P3 or P5 generated by pressure sensor 135-3 or pressure sensor 135-5 to determine the pressure Pmerge of the gas in chamber 150.

According to one embodiment, the controller 140 determines the volume of gas in chamber 130-2 using isothermal ideal gas laws as follows:

$$P_1 V_1 = P_2 V_2 \quad \text{(equation 6)}$$

For:

$V_{pc}$=Unknown volume of the chamber 130-2 of diaphragm pump 130 (left IPC)

$V_{com}$=the known volume of the chamber 150 (Common Tank)

$P_{pc}$=pressure of the chamber 130-2 Left IPC at point [4]

$P_{com}$=pressure of the chamber 150 (Common Tank) at point [3]

$P_{merge} = P_{pc} = P_{com}$ pressure when the two chambers (130-2 and 150) are equalized at point [5]

$$V_{pc} P_{pc} + V_{com} P_{com} = V_{pc} P_{merge} + V_{com} P_{merge} \quad \text{(equation 7)}$$

$$\vdots$$

$$V_{pc} = V_{com} \frac{P_{merge} - P_{com}}{P_{pc} - P_{merge}} \quad \text{(equation 8)}$$

An isothermal calculation assumes that all transient thermal effects in the system have had time to dissipate. This dissipation can take on the order of seconds to occur, depending on the details of the system. If the volume calculation is performed prior to the system returning to thermal equilibrium, the residual temperature differences will introduce errors in the volume calculation, which will in turn cause errors in the resultant flow rate calculation.

In accordance with one embodiment, in order to achieve the range of flow rates required in an infusion pump system, and to minimize errors due to volume changes during the measurement cycle, the current embodiment can be configured to calculate a volume of fluid pumped to the target recipient 108 before the transient thermal effects have dissipated. In order to maintain volume calculation accuracy, embodiments herein take into account thermal effects to produce a more accurate fluid delivery rate.

In one embodiment, the temperature changes in the gas happen too fast to be measured by standard thermal sensors. In other words, thermal sensors may not be able to accurately measure fast changing temperatures of the gases in tank 150, chamber 130-2, etc., during a respective pressure changes shown in graph 600. To address this issue, one embodiment herein includes estimating temperatures of the volumes of interest to calculate an actual fluid delivery rate. As mentioned, the temperature sensor 152 measures an average temperature of gas in the common tank 150. However, due to its thermal mass, the temperature sensor 152 may not be able to accurately reflect an actual temperature of gas in chamber 150.

There are a number of parameters that affect the temperature of the gases in the different volumes (e.g., tank 150, chamber 130-2, etc.) over time. For example, thermal changes come primarily from 3 sources in the pneumatic system:

1. Adiabatic heating or cooling due to pressure changes in the chamber
2. Heat transfer between the gas and the chamber wall
3. Volume change due to flow rate out of the IPC chamber One embodiment herein includes modeling the fluid delivery system 100 to accurately estimate the temperature of the chambers of interest. For example, as mentioned, the change in pressure of chambers (such as pump chamber 130-2 and chamber 150) as shown and discussed with respect to FIG. 6 causes the temperature of the pump chamber 130-2 and the common tank 150 to vary. More specifically, between point 1 and point 2 in FIG. 6, the pressure of the common tank 150 drops significantly, causing the temperature of the gas, Tcom, in chamber 150 (common tank) to drop. As previously discussed, the pressure of gas in the respective chambers (e.g., P5, P3, etc.) is continuously and accurately measured using respective pressure sensors 135-5, 135-3, etc.

In one embodiment, a first model is used to estimate temperature changes in the chambers due to adiabatic heating and/or cooling. In other words, any suitable equations can be used to determine a change in the temperature of the gases in the chambers as a result of the pressures changing. Increasing a pressure of a gas causes an increase in temperature; decreasing a pressure of a gas causes a decrease in temperature.

Another parameter affecting the temperature of the gases in the chambers is the thermal characteristics of the chambers themselves and conduits in between. The dark lines in FIG. 2 represent conduits interconnecting the different components in fluid delivery system 100. For example, the dark line extending between diaphragm pump 130 and valve 160-5 represents a conduit; the dark line between valve 160-5 in chamber 150 represents a conduit; and so on. Via respective conduits, each of the components (such as check valve 125-1, diaphragm pump 130, valve 160-5, etc.) in fluid delivery system 100 are interconnected.

According to embodiments herein, the thermal properties of the chambers (e.g., common tank 150, pump chamber 130-2, etc.) can be characterized and modeled to identify how quickly they sink or source heat when there is a change in temperature caused by a change in pressure. As an example, and as discussed, the reduction in the pressure of a tank can cause the temperature of the gas in the tank to decrease. The temperature of the tank itself may be higher in magnitude than the temperature of the gas, resulting in a flow of heat from the tank or chamber to the gas therein. Thermal flow causes the temperature of the gas in the chamber to eventually become the substantially the same as the temperature in the respective tank over time. Conversely, an increase in pressure of the tank can cause the temperature to increase. The flow of heat from gas to the tank or chamber decreases the temperature of the gas.

One embodiment herein includes estimating the temperature of the gas and taking into account thermal heat flow using a respective thermal model. The thermal model takes into account the transfer of heat from the gas to the respective chamber or tank and/or a transfer of heat from the respective chamber or tank to the gas. The heat transfer will likely vary depending on the type of material used to fabricate the tanks and respective interconnections. Certain material such as metal will be more thermally conductive; material such as plastic will be less thermally conductive.

As discussed above, the changes in the temperature of the gases due to changes in pressure are deterministic and thus can be accurately estimated. However, the flow of energy from tank to gas or from gas to tank will impact the temperature. Embodiments herein include producing a more accurate estimate of temperature by taking into account these flows of energy at different times based on thermal modeling.

Another factor affecting the temperatures of the gases in the chambers is the volume of the pump chamber 130-2 and how quickly it changes over time due to pumping of the fluid in the diaphragm pump chamber to the target recipient. For example, if the fluid in the pump chamber 130-2 is pumped at a very slow rate to target recipient 108, then volume change effects are minor or potentially negligible. Conversely, if the fluid in pump chamber 130-1 is pumped at a relatively high rate to the target recipient 108, then the volume change effects become more significant. As discussed herein, embodiments herein take into account the volume changes.

In one embodiment, the controller 140 generates the estimation of temperatures at discrete points in time such as between one second and one nanosecond. For each time step (i.e., each discrete time of producing an estimation of temperature) of the control system, the change in temperature due to those three sources is calculated for each pneumatic volume using the measured pressure as an input. The components (e.g., adiabatic effects, heat transfer effects, volume change effects) can be measured individually and/or in combination to produce a respective estimated temperature.

In the following equations subscripts 'i' and 'j' are used to denote each of the pneumatic volumes 130-2, 150, 170-1, 170-2. The subscript 'i' represents the chamber for which the temperature is being estimated; the subscript 'j' represents the associated chamber. For example, when estimating a temperature for the pump chamber 130-2, the subscript 'i' represents the pump chamber 130-2; subscript 'j' represents the common tank 150. When estimating a temperature for the common tank 150, the subscript 'i' represents the common tank 150; subscript 'j' represents the pump chamber 130-2, and so on.

By way of a non-limiting example, the temperature at time (n+1) is then calculated based on that change rate:

$$\frac{dT_n}{dt} = \text{(Heat Transfer Effects)} + \text{(Pressure Change Effects)} + \text{(Volume Change Effects)} \quad \text{(equation 9)}$$

$$T_{n+1} = T_n + dt \frac{dT_n}{dt} \quad \text{(equation 10)}$$

Heat transfer effects are based on the temperature of the gas in the chamber, the temperature of the chamber wall, and the heat transfer coefficient between the two. For example, in one embodiment:

$$\text{Heat Transfer Effects } H(T_{wall} - T_i) \quad \text{(equation 11)}$$

$T_i$ = last estimation of temperature for chamber i
H = heat transfer coefficient
$T_{wall}$ = ambient temperature $T_{tc}$ as sensed by temperature sensor 152

Pressure change effects are based on the mass flow from once chamber to another due to pressure differential between the two chambers:

$$Q_{ij} = C_{ij} A_{ij} \sqrt{2\rho_i (P_i - P_j)} \quad \text{(equation 12)}$$

$$Q_{in} = \sum_j Q_{ji} \quad \text{(equations 13 and 14)}$$

$$Q_{out} = \sum_j Q_{ij}$$

$$\text{Pressure Change Effects} = \frac{1}{M_i C_v} \left[ C_p \sum_j T_j Q_{ji} - C_p T_i Q_{out} - C_v T_i (Q_{in} - Q_{out}) \right] \quad \text{(equation 15)}$$

Where:
$M_i$ = mass of gas in chamber i;
$Q_{ij}$ is the mass flow rate from chamber i to chamber j.
$C_{ij}$ is the discharge coefficient of the valve between chamber i and j
$A_{ij}$ is the area of the orifice of the valve between chamber i and j
$\rho_i$ is the density of the gas in chamber i Volume change effects are based on any changes in actual volume of the chamber in question. In one embodiment, this effect only applies to chamber 130-2, which can change size due to motion of membrane 127.

$$\text{Volume Change Effects} = \left( \frac{C_p}{C_v} - 1 \right) \cdot \frac{T_i}{V_i} \frac{dV_i}{dt} \quad \text{(equation 16)}$$

Where:
V = volume
Cv = specific heat at constant volume
Cp = specific heat at constant pressure The estimated temperature curves through the pumping and measurement cycles can be seen in FIGS. 5a, 5b, and 6.

In this method the control system has an estimated temperature for each gas chamber that can be used in a modified ideal gas law volume calculation that takes temperature into account:

$$V_{pc} = V_{com} \frac{\left(\frac{P_{com2}}{T_{com2}} - \frac{P_{com1}}{T_{com1}}\right)}{\left(\frac{P_{pc1}}{T_{pc1}} - \frac{P_{pc2}}{T_{pc2}}\right)}$$ (equation 17)

Where:
$V_{pc}$=Unknown volume of the chamber 130-2 of diaphragm pump 130 (e.g., Left IPC)
$V_{com}$=the known volume of the chamber 150
$P_{com1}$=pressure $P_3$ from pressure sensor 135-3 of the chamber 150 at point [3]
$P_{com2}$=pressure $P_3$ from pressure sensor 135-3 of the chamber 150 at point [5]
$P_{pc1}$=pressure $P_5$ from pressure sensor 135-5 of the chamber 130-2 at point [4]
$P_{pc2}$=pressure $P_5$ from pressure sensor 135-5 of the chamber 130-2 at point [5]
$T_{com1}$=estimated temperature of the chamber 150 at point [3A]
$T_{com2}$=estimated temperature of the chamber 150 at point [5A1]
$T_{pc1}$=estimated temperature of the chamber 130-2 at point [4A]
$T_{pc2}$=estimated temperature of the chamber 130-2 at point [5A2]

As previously discussed, the volume of the chamber 130-1 can be calculated by subtracting the calculated VPC (e.g., volume of the pumping chamber 130-2) from the total volume of the diaphragm pump 130. The total volume of the diaphragm pump 130 is equal to the volume of chamber 130-1 plus the volume of chamber 130-2 and is a known quantity.

In a further embodiment, the volume of chamber 130-1 is not calculated, and flow rate is calculated by simply taking the difference in volume between subsequent calculations of the volume of chamber 130-2. In other words, the change in volume of pump chamber 130-2 over time is indicative of a pumping flow rate and can be used as a basis to calculate the flow rate. The controller 140 can be configured to precisely determine a respective flow rate of delivering fluid from chamber 130—one of diaphragm pump 130 based on the multiple measurements taken at times C, D, E, etc., in FIG. 5b. The flow rate=(change in volume of fluid in chamber 130-1)/(range of delivery time).

Using a temperature-corrected volume calculation (based on estimation of gas temperatures as described herein) allows the system to have a measure sequence that happens on the order of 80 milliseconds, rather than on the order of seconds while maintaining calculation accuracy.

Figure 7:
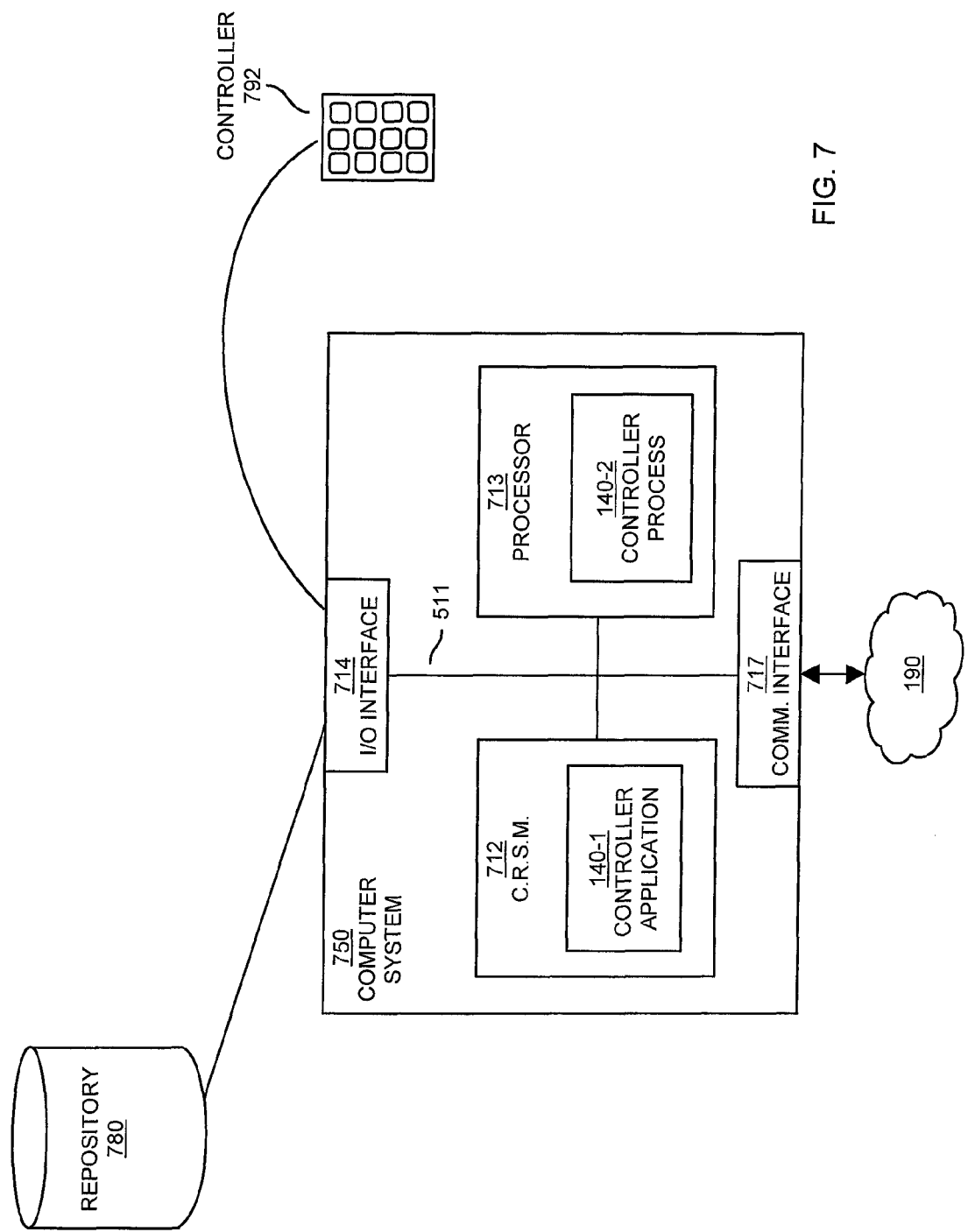
FIG. 7 is a diagram illustrating an example computer architecture in which to execute any of the functionality according to embodiments herein.

FIG. 7 is an example block diagram of a computer device for implementing any of the operations as discussed herein according to embodiments herein.

In one embodiment, fluid delivery system 100 includes a computer system 750 to execute controller 140.

As shown, computer system 750 of the present example includes an interconnect 711, a processor 713 (such as one or more processor devices, computer processor hardware, etc.), computer readable storage medium 712 (such as hardware storage to store data), I/O interface 714, and communications interface 717.

Interconnect 711 provides connectivity amongst processor 713, computer readable storage media 712, I/O interface 714, and communication interface 717.

I/O interface 714 provides connectivity to a repository 780 and, if present, other devices such as a playback device, display screen, input resource 792, a computer mouse, etc.

Computer readable storage medium 712 (such as a non-transitory hardware medium) can be any hardware storage resource or device such as memory, optical storage, hard drive, rotating disk, etc. In one embodiment, the computer readable storage medium 712 stores instructions executed by processor 713.

Communications interface 717 enables the computer system 750 and processor 713 to communicate over a resource such as network 190 to retrieve information from remote sources and communicate with other computers. I/O interface 714 enables processor 713 to retrieve stored information from repository 780.

As shown, computer readable storage media 712 is encoded with controller application 140-1 (e.g., software, firmware, etc.) executed by processor 713. Controller application 140-1 can be configured to include instructions to implement any of the operations as discussed herein.

During operation of one embodiment, processor 713 (e.g., computer processor hardware) accesses computer readable storage media 712 via the use of interconnect 711 in order to launch, run, execute, interpret or otherwise perform the instructions in controller application 140-1 stored on computer readable storage medium 712.

Execution of the controller application 140-1 produces processing functionality such as controller process 140-2 in processor 713. In other words, the controller process 140-2 associated with processor 713 represents one or more aspects of executing controller application 140-1 within or upon the processor 713 in the computer system 750.

Those skilled in the art will understand that the computer system 750 can include other processes and/or software and hardware components, such as an operating system that controls allocation and use of hardware resources to execute controller application 140-1.

In accordance with different embodiments, note that computer system may be any of various types of devices, including, but not limited to, a wireless access point, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. In one non-limiting example embodiment, the computer system 850 resides in fluid delivery system 100. However, note that computer system 850 may reside at any location or can be included in any suitable resource in network environment 100 to implement functionality as discussed herein.

Functionality supported by the different resources will now be discussed via flowcharts in FIGS. 8, 9, and 10. Note that the steps in the flowcharts below can be executed in any suitable order.

Figure 8:
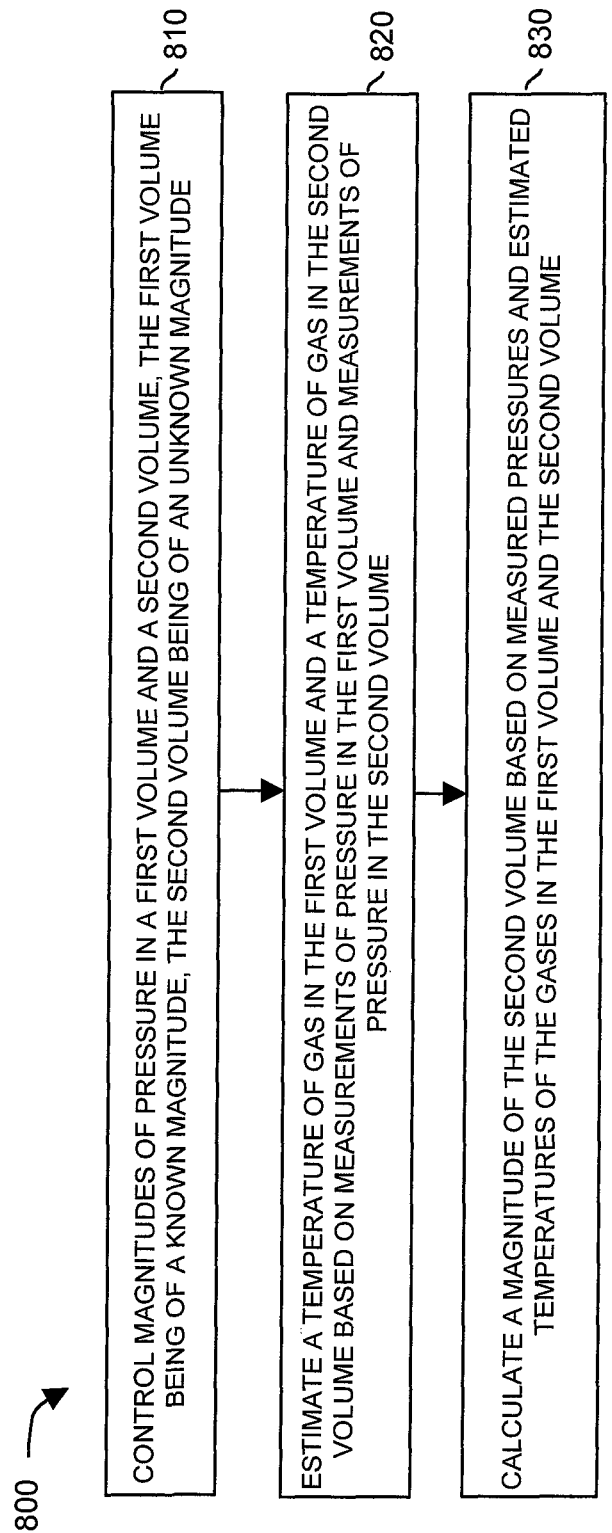
FIGS. 8-10 are example diagrams illustrating methods facilitating flow control measurement and management according to embodiments herein.

FIG. 8 is a flowchart 800 illustrating an example method according to embodiments. Note that there will be some overlap with respect to concepts as discussed above.

In processing block 810, the controller 140 controls magnitudes of pressure in a first volume (such as chamber 150) and a second volume (such as chamber 130-2). The first volume is of a known magnitude (i.e., size). The second volume is of an unknown magnitude (i.e., size).

In processing block 820, the controller 140 estimates a temperature of gas in the first volume and a temperature of gas in the second volume based on measurements of pressure in the first volume and measurements of pressure in the second volume.

In processing block 830, the controller 140 calculates a magnitude of the second volume based on measured pressures of the gases and estimated temperatures of gases in the first volume and the second volume.

Figure 9:
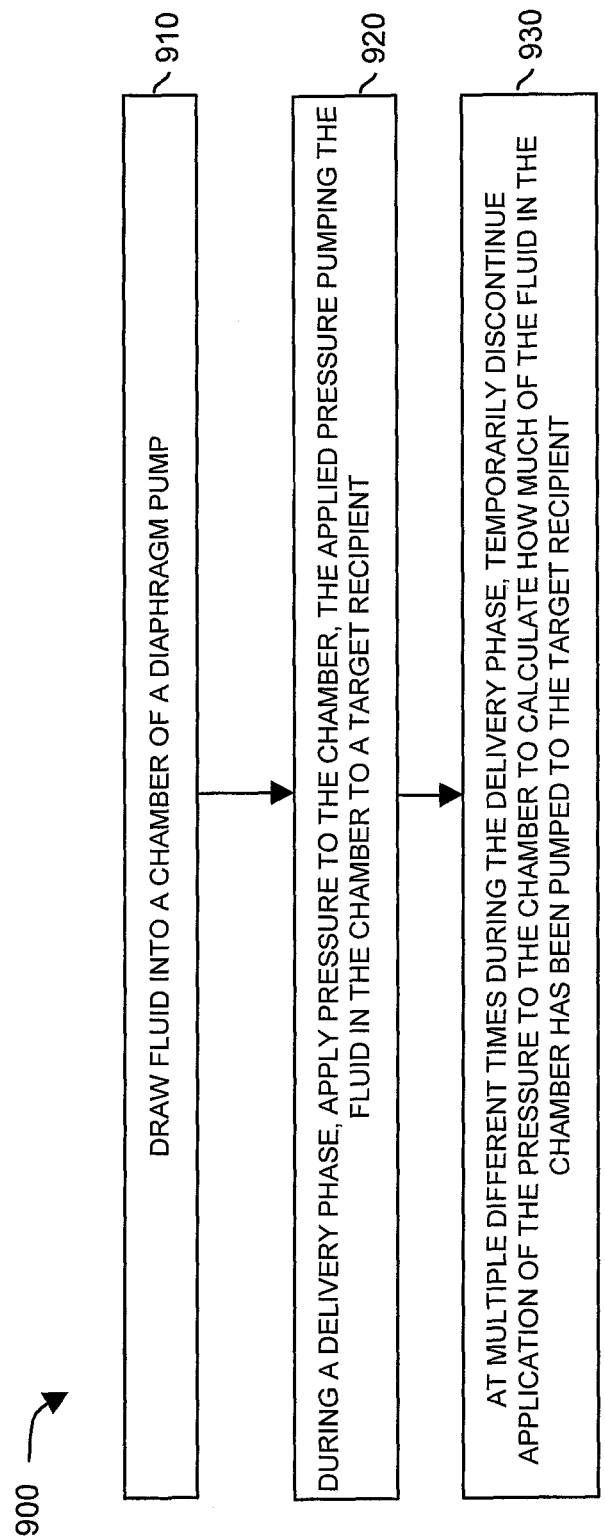

FIG. 9 is a flowchart 900 illustrating an example method according to embodiments. Note that there will be some overlap with respect to concepts as discussed above.

In processing block 910, the controller 140 draws fluid into a chamber of a diaphragm pump 130.

In processing block 920, during a delivery phase, the controller 140 applies pressure to the chamber 130-1. The applied pressure pumps the fluid in the chamber 130-1 to a target recipient 108.

In processing block 930, at multiple different times during the delivery phase, the controller 140 temporarily discontinues application of the pressure to the chamber 130-2 to calculate how much of the fluid in the chamber 130-1 has been pumped to the target recipient 108.

Figure 10:
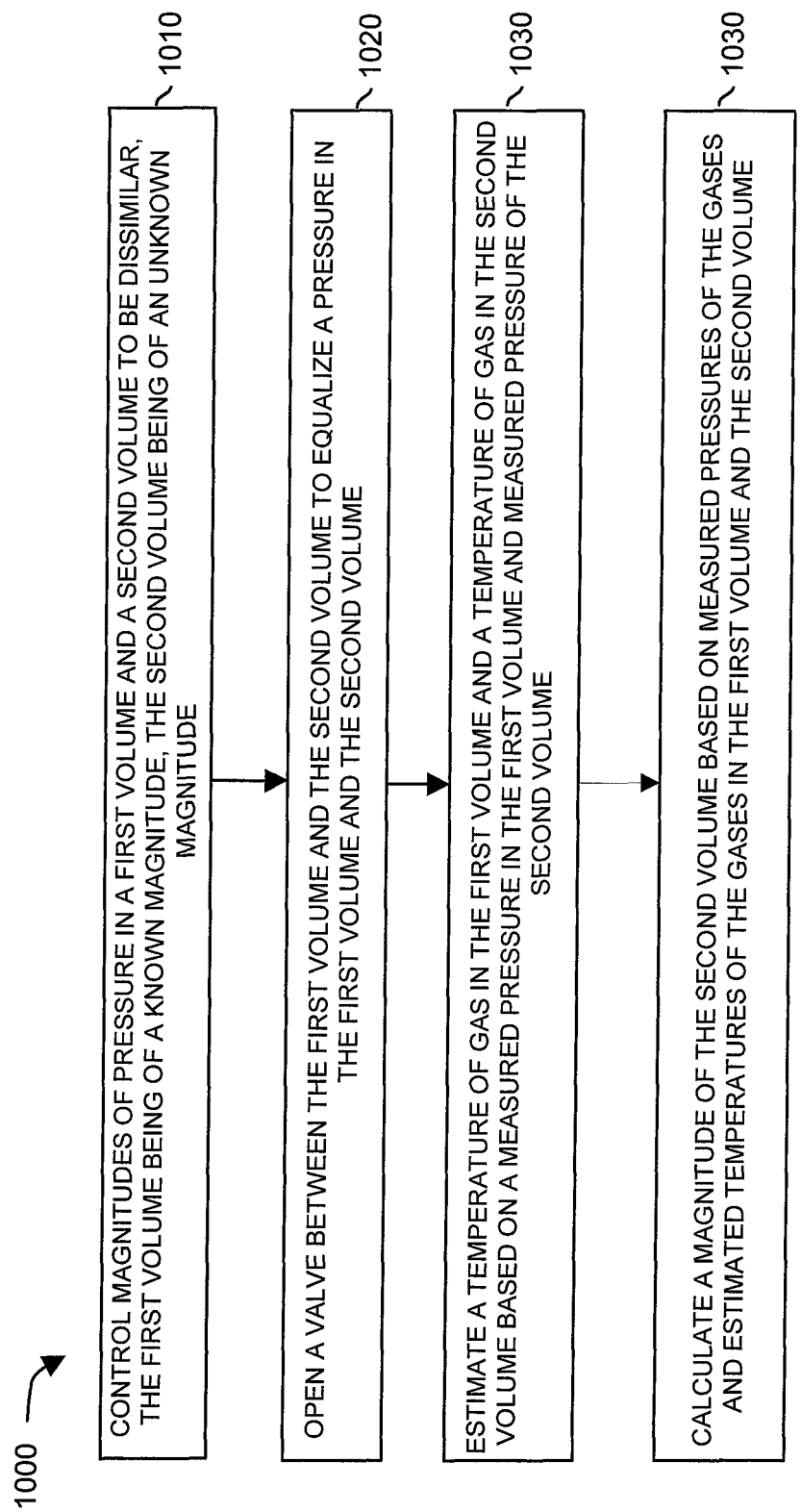

FIG. 10 is a flowchart 1000 illustrating an example method according to embodiments. Note that there will be some overlap with respect to concepts as discussed above.

In processing block 1010, the controller 140 controls magnitudes of pressure in a first volume (such as chamber 150) and a second volume (such as chamber 130-2) to be dissimilar. The first volume is of known magnitude. The second volume is of unknown magnitude.

In processing block 1020, the controller 140 initiates opening a valve 160-5 (while other valves are closed) between the first volume and the second volume to equalize a pressure in the first volume and the second volume.

In processing block 1030, the controller 140 estimates a temperature of gas in the first volume and a temperature of gas in the second volume based on a measured pressure in the first volume and measured pressure of the second volume.

In processing block 1040, the controller 140 calculates a magnitude of the second volume based on measured pressures of the gases and estimated temperatures of the gases in the first volume and the second volume.

Note again that techniques herein are well suited for use in fluid delivery systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
    drawing fluid into a chamber of a diaphragm pump;
    during a delivery phase, applying pressure to the chamber, the applied pressure pumping the fluid in the chamber to a target recipient; and
    at multiple different times during the delivery phase, temporarily discontinuing application of the pressure to the chamber to calculate how much of the fluid in the chamber has been pumped to the target recipient,
    the method further comprising:
        calculating an amount of fluid in the chamber at the multiple different times during the delivery phase; and
        calculating a flow rate of delivering the fluid in the chamber to the target recipient based on the calculated amount of fluid in the chamber at the multiple different times during the delivery phase.

2. The method as in claim 1, wherein applying pressure to the chamber includes:
    applying a substantially constant pressure to the chamber to evacuate the fluid from the chamber into a conduit that conveys the fluid to the target recipient.

3. The method as in claim 1 further comprising:
    comparing the calculated flow rate to a desired flow rate; and
    in response to detecting that a difference between the calculated flow rate and the desired flow rate is greater than a threshold value, adjusting a flow rate of the fluid from the chamber to the target recipient to be nearer to the desired flow rate.

4. The method as in claim 3, wherein adjusting the flow rate includes:
adjusting a magnitude of the pressure applied to the chamber during the delivery phase.

5. The method as in claim 4, wherein adjusting the flow rate includes:
adjusting resistance of an in-line flow resistor disposed between the chamber and the target recipient.

6. The method as in claim 1, wherein discontinuing application of the pressure to the chamber causes a pumping of the fluid in the chamber to the recipient to substantially stop.

7. The method as in claim 1 further comprising:
subsequent to discontinuing application of the pressure to the chamber, resuming application of the pressure to the chamber, resumption of applying the pressure causing the fluid in the chamber to flow to the recipient again.

8. The method as in claim 1, wherein discontinuing application of the pressure to the chamber includes controlling magnitudes of pressure in the chamber and a gas reservoir tank to be dissimilar, a volume of the reservoir tank being of a known magnitude, a volume of the chamber being of an unknown magnitude, the method further comprising:
opening a valve between the reservoir tank and the chamber to substantially equalize a pressure of gas in the reservoir tank and the chamber;
estimating a temperature of gas in the reservoir tank and a temperature of gas in the chamber based on a measured pressure in the reservoir tank and measured pressure of the chamber; and
calculating how much of the fluid remains in the chamber based at least in part on measured pressures of the gases and the estimated temperatures of the gases in the reservoir tank and the chamber.

9. A method comprising:
drawing fluid into a chamber of a diaphragm pump;
during a delivery phase, applying pressure to the chamber, the applied pressure pumping the fluid in the chamber to a target recipient; and
at multiple different times during the delivery phase, temporarily discontinuing application of the pressure to the chamber to calculate how much of the fluid in the chamber has been pumped to the target recipient;
wherein discontinuing application of the pressure to the chamber includes controlling magnitudes of pressure in the chamber and a gas reservoir tank to be dissimilar, a volume of the reservoir tank being of a known magnitude, a volume of the chamber being of an unknown magnitude, the method further comprising:
opening a valve between the reservoir tank and the chamber to substantially equalize a pressure of gas in the reservoir tank and the chamber;
estimating a temperature of gas in the reservoir tank and a temperature of gas in the chamber based on a measured pressure in the reservoir tank and measured pressure of the chamber; and
calculating how much of the fluid remains in the chamber based at least in part on measured pressures of the gases and the estimated temperatures of the gases in the reservoir tank and the chamber.

10. The method as in claim 9 further comprising:
calculating how much of the fluid has been pumped to the target recipient based at least in part on how much of the fluid drawn into the chamber remains in the chamber after applying the pressure.

11. The method as in claim 9, wherein applying pressure to the chamber includes:
applying a substantially constant pressure to the chamber to evacuate the fluid from the chamber into a conduit that conveys the fluid to the target recipient.

12. The method as in claim 9, wherein discontinuing application of the pressure to the chamber causes a pumping of the fluid in the chamber to the recipient to substantially stop.

13. The method as in claim 9 further comprising:
subsequent to discontinuing application of the pressure to the chamber, resuming application of the pressure to the chamber, resumption of applying the pressure causing the fluid in the chamber to flow to the recipient again.

14. A fluid delivery system comprising:
a diaphragm pump; and
a controller in controllable communication with the diaphragm pump, the controller operable to:
draw fluid into a chamber of the diaphragm pump;
during a delivery phase, apply pressure to the chamber, the applied pressure pumping the fluid in the chamber to a target recipient; and
at multiple different times during the delivery phase, temporarily discontinue application of the pressure to the chamber to calculate how much of the fluid in the chamber has been pumped to the target recipient;
calculate an amount of fluid in the chamber at the multiple different times during the delivery phase; and
calculate a flow rate of delivering the fluid in the chamber to the target recipient based on the calculated amount of fluid in the chamber at the multiple different times during the delivery phase.

15. The fluid delivery system as in claim 14, wherein the controller is further operable to:
apply a substantially constant pressure to the chamber to evacuate the fluid from the chamber into a conduit that conveys the fluid to the target recipient.

16. The fluid delivery system as in claim 14, wherein the controller is further operable to:
compare the calculated flow rate to a desired flow rate; and
in response to detecting that a difference between the calculated flow rate and the desired flow rate is greater than a threshold value, adjust a flow rate of the fluid from the chamber to the target recipient to be nearer to the desired flow rate.

17. The fluid delivery system as in claim 16, wherein the controller is further operable to:
adjust a magnitude of the pressure applied to the chamber during the delivery phase.

18. The fluid delivery system as in claim 17, wherein the controller is further operable to:
adjust resistance of an in-line flow resistor disposed between the chamber and the target recipient.

19. The fluid delivery system as in claim 14 further comprising:
a gas reservoir tank;
a valve disposed between the chamber and the gas reservoir tank; and
wherein the controller is further operable to:
control magnitudes of pressure in the chamber and the gas reservoir tank to be dissimilar, a volume of the gas reservoir tank being of a known magnitude, a volume of the chamber being of an unknown magnitude;

open the valve between the gas reservoir tank and the chamber to substantially equalize a pressure of gas in the gas reservoir tank and the chamber;

estimate a temperature of gas in the gas reservoir tank and a temperature of gas in the chamber based on a measured pressure in the gas reservoir tank and measured pressure of the chamber; and calculate how much of the fluid remains in the chamber based at least in part on measured pressures of the gases and the estimated temperatures of the gases in the gas reservoir tank and the chamber.

20. The fluid delivery system as in claim 19, wherein the controller is further operable to:

calculate how much of the fluid has been pumped to the target recipient based at least in part on how much of the fluid drawn into the chamber remains in the chamber after applying the pressure.

21. The fluid delivery system as in claim 14, wherein the controller is further operable to discontinue application of the pressure to the chamber to substantially stop a pumping of the fluid in the chamber to the recipient.

22. The fluid delivery system as in claim 14, wherein the controller is further operable to:

subsequent to discontinuing application of the pressure to the chamber, resume application of the pressure to the chamber, resumption of applying the pressure causing the fluid in the chamber to flow to the recipient again.

23. Computer-readable hardware storage having instructions stored thereon, the instructions, when carried out by computer processor hardware, causes the computer processor hardware to perform operations of:

drawing fluid into a chamber of a diaphragm pump;

during a delivery phase, applying pressure to the chamber, the applied pressure pumping the fluid in the chamber to a target recipient; and at multiple different times during the delivery phase, temporarily discontinuing application of pressure to the chamber to calculate how much of the fluid in the chamber has been pumped to the target recipient;

calculating an amount of fluid in the chamber at the multiple different times during the delivery phase; and calculating a flow rate of delivering the fluid in the chamber to the target recipient based on the calculated amount of fluid in the chamber at the multiple different times during the delivery phase.

24. A fluid delivery system comprising:

a diaphragm pump including a chamber;

a gas reservoir tank;

a valve disposed between the chamber and the gas reservoir tank and a controller in controllable communication with the diaphragm pump, the controller operable to:

draw fluid into the chamber of the diaphragm pump;

during a delivery phase, apply pressure to the chamber, the applied pressure pumping the fluid in the chamber to a target recipient; and at multiple different times during the delivery phase, temporarily discontinue application of the pressure to the chamber to calculate how much of the fluid in the chamber has been pumped to the target recipient;

wherein the controller is further operable to:

control magnitudes of pressure in the chamber and the gas reservoir tank to be dissimilar, a volume of the gas reservoir tank being of a known magnitude, a volume of the chamber being of an unknown magnitude;

open the valve between the gas reservoir tank and the chamber to substantially equalize a pressure of gas in the gas reservoir tank and the chamber;

estimate a temperature of gas in the gas reservoir tank and a temperature of gas in the chamber based on a measured pressure in the gas reservoir tank and measured pressure of the chamber; and calculate how much of the fluid remains in the chamber based at least in part on measured pressures of the gases and the estimated temperatures of the gases in the gas reservoir tank and the chamber.

25. The fluid delivery system as in claim 24, wherein the controller is further operable to:

apply a substantially constant pressure to the chamber to evacuate the fluid from the chamber into a conduit that conveys the fluid to the target recipient.

26. The fluid delivery system as in claim 24, wherein discontinuing application of the pressure to the chamber causes a pumping of the fluid in the chamber to the recipient to substantially stop.

27. The fluid delivery system as in claim 24, wherein the controller is further operable to:

subsequent to discontinuing application of the pressure to the chamber, resume application of the pressure to the chamber, resumption of applying the pressure causing the fluid in the chamber to flow to the recipient again.

* * * * *